United States Patent
Akella et al.

(10) Patent No.: US 11,054,811 B2
(45) Date of Patent: Jul. 6, 2021

(54) SYSTEMS AND METHODS FOR LINE BALANCING

(71) Applicant: Drishti Technologies, Inc., Palo Alto, CA (US)

(72) Inventors: Prasad Narasimha Akella, Palo Alto, CA (US); Krishnendu Chaudhury, Saratoga, CA (US); Sameer Gupta, Palot Alto, CA (US); Ananth Uggirala, Mountain View, CA (US)

(73) Assignee: Drishti Technologies, Inc., Palo Alto, CA (US)

( * ) Notice: Subject to any disclaimer, the term of this patent is extended or adjusted under 35 U.S.C. 154(b) by 0 days.

(21) Appl. No.: 16/181,112

(22) Filed: Nov. 5, 2018

(65) Prior Publication Data

US 2019/0137979 A1    May 9, 2019

Related U.S. Application Data

(60) Provisional application No. 62/581,541, filed on Nov. 3, 2017.

(51) Int. Cl.
   *G05B 19/418*    (2006.01)
   *G06Q 10/06*    (2012.01)
   (Continued)

(52) U.S. Cl.
   CPC ... *G05B 19/41835* (2013.01); *G05B 19/4183* (2013.01); *G06F 9/4498* (2018.02);
   (Continued)

(58) Field of Classification Search
   CPC .... G05B 19/41865; G05B 2219/32267; G05B 2219/32015; G05B 19/41805;
   (Continued)

(56) References Cited

U.S. PATENT DOCUMENTS 5,093,794 A * 3/1992 Howie ............... G06Q 10/06
                                                     700/100
5,177,688 A * 1/1993 Rentschler ....... G05B 19/41835
                                                     700/101
(Continued)

FOREIGN PATENT DOCUMENTS

EP    2045679 A1 * 4/2009  ....... G05B 19/41865
EP    2626757        8/2013
(Continued)

OTHER PUBLICATIONS

Sepp Hochreiter & Jurgen Schmidhuber, Long Short-Term memory, Neural Computation, vol. 9, Issue 8, p. 1735-1780, Nov. 15, 1997.
(Continued)

*Primary Examiner* — Darrin D Dunn

(57) ABSTRACT

In various embodiments, a method includes receiving one or more sensor streams with an engine. The engine identifies one or more actions that are performed at first and second stations of a plurality of stations within the sensor stream(s). The received sensor stream(s) and identified one or more actions performed at the first and second stations are stored in a data structure. The identified one or more actions are mapped to the sensor stream(s). The engine characterizes each of the identified one or more actions performed at each of the first and second stations to produce determined characterizations thereof. Based on one or more of the determined characterizations, automatically producing a recommendation, either dynamically or post-facto, to move at least one of the identified one or more actions performed at one of the stations to another station to reduce cycle time.

24 Claims, 18 Drawing Sheets

(51) Int. Cl.
| | |
|---|---|
| G06F 16/9035 | (2019.01) |
| G06F 16/904 | (2019.01) |
| G06F 16/2455 | (2019.01) |
| G06F 30/20 | (2020.01) |
| G06F 30/23 | (2020.01) |
| G06N 3/04 | (2006.01) |
| G06N 3/08 | (2006.01) |
| G06F 16/23 | (2019.01) |
| G06F 11/07 | (2006.01) |
| G06N 20/00 | (2019.01) |
| G06K 9/00 | (2006.01) |
| G06F 16/22 | (2019.01) |
| G06N 3/00 | (2006.01) |
| G06F 9/48 | (2006.01) |
| G06F 16/901 | (2019.01) |
| G06N 7/00 | (2006.01) |
| G06F 9/448 | (2018.01) |
| G06T 19/00 | (2011.01) |
| G09B 19/00 | (2006.01) |
| G06F 111/10 | (2020.01) |
| G06F 111/20 | (2020.01) |
| G06K 9/62 | (2006.01) |
| G01M 99/00 | (2011.01) |
| G06Q 50/26 | (2012.01) |
| B25J 9/16 | (2006.01) |
| G05B 19/423 | (2006.01) |
| G16H 10/60 | (2018.01) |
| G06Q 10/08 | (2012.01) |

(52) U.S. Cl.
CPC .......... *G06F 9/4881* (2013.01); *G06F 11/079* (2013.01); *G06F 11/0721* (2013.01); *G06F 16/2228* (2019.01); *G06F 16/2365* (2019.01); *G06F 16/24568* (2019.01); *G06F 16/904* (2019.01); *G06F 16/9024* (2019.01); *G06F 16/9035* (2019.01); *G06F 30/20* (2020.01); *G06F 30/23* (2020.01); *G06K 9/00335* (2013.01); *G06N 3/008* (2013.01); *G06N 3/04* (2013.01); *G06N 3/0445* (2013.01); *G06N 3/0454* (2013.01); *G06N 3/08* (2013.01); *G06N 3/084* (2013.01); *G06N 7/005* (2013.01); *G06N 20/00* (2019.01); *G06Q 10/06* (2013.01); *G06Q 10/06316* (2013.01); *G06Q 10/06393* (2013.01); *G06Q 10/06395* (2013.01); *G06Q 10/06398* (2013.01); *G06Q 10/063112* (2013.01); *G06T 19/006* (2013.01); *G09B 19/00* (2013.01); *B25J 9/1664* (2013.01); *B25J 9/1697* (2013.01); *G01M 99/005* (2013.01); *G05B 19/41865* (2013.01); *G05B 19/423* (2013.01); *G05B 2219/32056* (2013.01); *G05B 2219/36442* (2013.01); *G06F 2111/10* (2020.01); *G06F 2111/20* (2020.01); *G06K 9/6262* (2013.01); *G06N 3/006* (2013.01); *G06Q 10/083* (2013.01); *G06Q 50/26* (2013.01); *G16H 10/60* (2018.01)

(58) Field of Classification Search
CPC ...... G05B 19/4183; G05B 2219/32258; G05B 2219/39167; G05B 2219/32056; G06F 9/4881; G06F 3/126
See application file for complete search history.

(56) References Cited

U.S. PATENT DOCUMENTS

| | | | | |
|---|---|---|---|---|
| 5,229,948 A * | 7/1993 | Wei | ............... | G05B 19/41885 700/99 |
| 5,615,138 A * | 3/1997 | Tanaka | ............... | G06Q 10/06 702/81 |
| 5,880,960 A * | 3/1999 | Lin | ............... | G06F 17/11 700/99 |
| 6,198,980 B1 * | 3/2001 | Costanza | ............... | G05B 19/41865 700/97 |
| 6,249,715 B1 * | 6/2001 | Yuri | ............... | G06Q 10/04 700/108 |
| 6,259,959 B1 * | 7/2001 | Martin | ............... | G06Q 10/06 700/99 |
| 6,263,253 B1 * | 7/2001 | Yang | ............... | G06Q 10/06 700/99 |
| 6,263,255 B1 * | 7/2001 | Tan | ............... | G05B 19/41845 700/106 |
| 6,349,237 B1 * | 2/2002 | Koren | ............... | B23Q 37/00 700/96 |
| 6,418,351 B1 * | 7/2002 | Martin | ............... | G06Q 10/06 700/108 |
| 6,591,153 B2 * | 7/2003 | Crampton | ............... | G06Q 10/06 700/103 |
| 6,622,055 B2 * | 9/2003 | Fan | ............... | G05B 19/41865 700/99 |
| 6,654,673 B2 * | 11/2003 | Ferguson | ............... | G06F 11/2294 701/31.4 |
| 6,763,277 B1 * | 7/2004 | Allen, Jr. | ............... | G05B 19/41865 700/100 |
| 6,829,514 B2 * | 12/2004 | Gyorfi | ............... | H05K 13/085 700/99 |
| 7,257,459 B1 * | 8/2007 | Qu | ............... | G05B 19/41865 700/101 |
| 7,349,751 B2 * | 3/2008 | Denton | ............... | G05B 19/41865 700/100 |
| 7,379,206 B2 * | 5/2008 | Gartstein | ............... | G06F 3/1204 358/1.9 |
| 7,558,638 B2 * | 7/2009 | Chang | ............... | G05B 19/4184 700/97 |
| 7,587,804 B2 * | 9/2009 | Steinhilper | ............... | G05B 19/41865 29/430 |
| 7,715,929 B2 * | 5/2010 | Skourup | ............... | G05B 17/02 340/3.1 |
| 7,809,457 B2 * | 10/2010 | Yuan | ............... | G05B 19/41865 700/101 |
| 8,019,467 B2 * | 9/2011 | Hongkham | ............... | H01L 21/67173 700/214 |
| 8,768,498 B2 * | 7/2014 | Hermann | ............... | G05B 23/0251 700/99 |
| 9,050,723 B1 * | 6/2015 | Elazary | ............... | G06F 11/0793 |
| 9,377,778 B2 * | 6/2016 | Crothers | ............... | G05B 19/4183 |
| 9,571,797 B2 * | 2/2017 | Kanehira | ............... | G06K 9/00771 |
| 9,623,560 B1 * | 4/2017 | Theobald | ............... | B25J 9/1676 |
| 9,734,569 B2 * | 8/2017 | Beach | ............... | G06T 7/0004 |
| 9,753,453 B2 * | 9/2017 | Benaim | ............... | G06F 30/00 |
| 10,022,870 B2 * | 7/2018 | Guerin | ............... | B25J 9/1664 |
| 10,108,829 B2 * | 10/2018 | Telling | ............... | G06K 7/10405 |
| 10,239,209 B2 * | 3/2019 | Kimoto | ............... | B25J 9/1671 |
| 10,545,489 B2 * | 1/2020 | Christensen | ............... | G05B 19/41865 |
| 2002/0026257 A1 * | 2/2002 | Newmark | ............... | G05B 19/41805 700/108 |
| 2002/0107600 A1 * | 8/2002 | Crampton | ............... | G06Q 10/06 700/100 |
| 2003/0097197 A1 * | 5/2003 | Parent | ............... | G05B 13/042 700/108 |
| 2003/0109950 A1 * | 6/2003 | Andrade, Jr. | ............... | G06Q 10/06 700/103 |
| 2003/0167238 A1 * | 9/2003 | Zeif | ............... | G05B 23/0267 705/400 |
| 2003/0225812 A1 * | 12/2003 | Nagashima | ............... | G05B 19/4147 718/102 |
| 2003/0229471 A1 | 12/2003 | Guralnik et al. | | |

(56) References Cited

U.S. PATENT DOCUMENTS

| | | | |
|---|---|---|---|
| 2003/0236585 A1* | 12/2003 | Kao | G05B 19/41865 700/108 |
| 2004/0148047 A1* | 7/2004 | Dismukes | G05B 19/41865 700/100 |
| 2005/0105765 A1 | 5/2005 | Han et al. | |
| 2006/0017821 A1* | 1/2006 | Garvey, III | H04N 5/77 348/231.3 |
| 2006/0136085 A1* | 6/2006 | Steinhilper | G05B 19/41865 700/111 |
| 2006/0155406 A1* | 7/2006 | Rossi | G05B 19/41865 700/99 |
| 2006/0212875 A1* | 9/2006 | Haller | G06F 9/4856 718/107 |
| 2006/0220839 A1* | 10/2006 | Fifolt | A61B 5/0002 340/539.12 |
| 2006/0224254 A1* | 10/2006 | Rumi | G05B 13/0275 700/28 |
| 2006/0241792 A1 | 10/2006 | Pretlove et al. | |
| 2006/0241793 A1* | 10/2006 | Skourup | G05B 17/02 700/83 |
| 2006/0271526 A1 | 11/2006 | Charnock et al. | |
| 2007/0043464 A1* | 2/2007 | Zeif | G05B 23/0267 700/108 |
| 2007/0168082 A1* | 7/2007 | Kim | B25J 9/1658 700/245 |
| 2007/0198135 A1* | 8/2007 | Chang | G05B 19/4184 700/300 |
| 2008/0034072 A1* | 2/2008 | He | H04L 41/5009 709/223 |
| 2008/0109114 A1* | 5/2008 | Orita | H02J 7/0027 700/248 |
| 2008/0123750 A1* | 5/2008 | Bronstein | H04N 19/17 375/240.24 |
| 2008/0154909 A1* | 6/2008 | Dam | G06F 16/90 |
| 2008/0188973 A1* | 8/2008 | Filev | G05B 23/0221 700/110 |
| 2009/0016599 A1 | 1/2009 | Eaton et al. | |
| 2009/0016600 A1 | 1/2009 | Eaton et al. | |
| 2009/0089227 A1 | 4/2009 | Sturrock et al. | |
| 2009/0099678 A1* | 4/2009 | Kurata | G05B 19/41865 700/106 |
| 2009/0112350 A1* | 4/2009 | Yuan | G05B 19/41835 700/117 |
| 2009/0138322 A1* | 5/2009 | Joyner | G06Q 10/06 705/7.38 |
| 2009/0157569 A1* | 6/2009 | Henby | G06Q 10/06 705/500 |
| 2009/0171492 A1* | 7/2009 | Qu | G06Q 10/06 700/101 |
| 2009/0204245 A1* | 8/2009 | Sustaeta | G05B 13/024 700/99 |
| 2010/0010879 A1* | 1/2010 | Roebke | G06Q 10/06 705/7.39 |
| 2010/0023147 A1* | 1/2010 | Knipfer | G06Q 10/087 700/96 |
| 2010/0082512 A1 | 4/2010 | Myerson et al. | |
| 2010/0191372 A1* | 7/2010 | Nihei | F16P 1/00 700/245 |
| 2011/0022212 A1* | 1/2011 | Nonaka | G05B 19/4184 700/108 |
| 2011/0043626 A1 | 2/2011 | Cobb et al. | |
| 2011/0055669 A1* | 3/2011 | DeHaan | G06F 11/0709 714/799 |
| 2011/0141266 A1* | 6/2011 | Fontanot | G05B 19/4183 348/86 |
| 2011/0179627 A1* | 7/2011 | Kondo | B23P 21/004 29/430 |
| 2011/0225018 A1* | 9/2011 | Reaume | G05B 19/41865 705/7.27 |
| 2012/0054764 A1* | 3/2012 | Bagheri | G06F 9/50 718/104 |
| 2012/0132313 A1* | 5/2012 | Bhatla | C40B 30/10 141/1 |
| 2012/0197898 A1 | 8/2012 | Pandey et al. | |
| 2012/0225413 A1 | 9/2012 | Kotranza et al. | |
| 2012/0327228 A1* | 12/2012 | Nomura | G08G 1/04 348/143 |
| 2013/0218340 A1* | 8/2013 | Hager | B25J 9/1671 700/257 |
| 2013/0290972 A1* | 10/2013 | Cherkasova | G06F 9/5066 718/103 |
| 2013/0307693 A1 | 11/2013 | Stone et al. | |
| 2013/0339923 A1 | 12/2013 | Xu et al. | |
| 2014/0037108 A1* | 2/2014 | Christoph | H03G 3/20 381/107 |
| 2014/0067108 A1* | 3/2014 | Pedigo | G05B 19/41865 700/108 |
| 2014/0079297 A1 | 3/2014 | Tadayon et al. | |
| 2014/0163730 A1* | 6/2014 | Mian | B25J 9/16 700/248 |
| 2014/0172357 A1 | 6/2014 | Heinonen | |
| 2014/0222813 A1 | 8/2014 | Yang et al. | |
| 2014/0247347 A1* | 9/2014 | McNeill | H04N 7/18 348/143 |
| 2014/0277593 A1 | 9/2014 | Nixon et al. | |
| 2014/0303767 A1* | 10/2014 | Klumpp | G05B 19/41845 700/105 |
| 2014/0326084 A1 | 11/2014 | Bhushan | |
| 2014/0337000 A1 | 11/2014 | Asenjo et al. | |
| 2014/0351819 A1* | 11/2014 | Shah | G06F 9/4887 718/103 |
| 2015/0098110 A1* | 4/2015 | Zeng | G06F 3/1263 358/1.15 |
| 2015/0110388 A1 | 4/2015 | Eaton et al. | |
| 2015/0116482 A1* | 4/2015 | Bronmark | H04N 5/23216 348/129 |
| 2015/0185729 A1* | 7/2015 | Kuffner, Jr. | G05B 19/4187 700/248 |
| 2015/0227138 A1* | 8/2015 | Gultekin | G06Q 10/06 700/111 |
| 2015/0234380 A1* | 8/2015 | Srikumar | G05B 19/4183 700/115 |
| 2015/0294143 A1* | 10/2015 | Wells | G06K 9/00369 348/159 |
| 2015/0321350 A1* | 11/2015 | Mian | B25J 9/16 700/257 |
| 2015/0364158 A1 | 12/2015 | Gupte et al. | |
| 2016/0085607 A1 | 3/2016 | Marr et al. | |
| 2016/0124399 A1* | 5/2016 | Su | G05B 11/01 700/275 |
| 2016/0132046 A1* | 5/2016 | Beoughter | G05B 19/4184 700/17 |
| 2016/0147569 A1* | 5/2016 | Cowling | G06F 16/22 718/104 |
| 2016/0148135 A1* | 5/2016 | Herron | G06Q 10/06312 705/7.22 |
| 2017/0004697 A1* | 1/2017 | Boerhout | G08B 21/18 |
| 2017/0008174 A1* | 1/2017 | Rosen | B25J 9/1697 |
| 2017/0021502 A1* | 1/2017 | Nusser | B25J 9/1687 |
| 2017/0023918 A1* | 1/2017 | Frazer | G05B 15/02 |
| 2017/0038762 A1* | 2/2017 | Canedo | G05B 19/406 |
| 2017/0057081 A1* | 3/2017 | Krohne | B25J 9/0084 |
| 2017/0098161 A1 | 4/2017 | Ellenbogen et al. | |
| 2017/0136627 A1* | 5/2017 | Takaichi | B25J 13/00 |
| 2017/0178311 A1* | 6/2017 | Pal | H04W 4/80 |
| 2017/0220032 A1* | 8/2017 | Ooba | G05B 19/41865 |
| 2017/0227950 A1* | 8/2017 | Kinoshita | G05B 13/0265 |
| 2017/0232613 A1 | 8/2017 | Ponulak et al. | |
| 2017/0243135 A1* | 8/2017 | Ooba | G05B 19/4185 |
| 2017/0248941 A1* | 8/2017 | Arita | G05B 23/027 |
| 2017/0252926 A1* | 9/2017 | Wise | B25J 9/1669 |
| 2017/0308052 A1* | 10/2017 | Kajiyama | G05B 19/402 |
| 2017/0315540 A1* | 11/2017 | Nishioka | G05B 19/406 |
| 2017/0343992 A1* | 11/2017 | Benaim | G05B 19/4183 |
| 2017/0371322 A1* | 12/2017 | Lake | H04W 4/50 |
| 2017/0374296 A1* | 12/2017 | Schmidt | G01J 5/10 |
| 2018/0001476 A1* | 1/2018 | Tan | B25J 9/1682 |

(56) References Cited

U.S. PATENT DOCUMENTS

| | | | |
|---|---|---|---|
| 2018/0024518 A1* | 1/2018 | Jin | G06Q 50/04 |
| | | | 112/217.2 |
| 2018/0046953 A1* | 2/2018 | Murakami | G06Q 10/0633 |
| 2018/0107174 A1* | 4/2018 | Takahashi | G05B 13/04 |
| 2018/0129192 A1* | 5/2018 | Murakami | G06Q 40/125 |
| 2018/0150066 A1* | 5/2018 | Chen | G05B 19/41865 |
| 2018/0172518 A1* | 6/2018 | Hiramatsu | G06T 7/0002 |
| 2018/0174084 A1* | 6/2018 | Murakami | G06Q 10/06311 |
| 2018/0189748 A1* | 7/2018 | Anderson | G06Q 10/20 |
| 2018/0191988 A1* | 7/2018 | Takahashi | H04N 5/44591 |
| 2018/0197131 A1* | 7/2018 | Grossman | G09B 5/06 |
| 2018/0197311 A1* | 7/2018 | Takizawa | B25J 9/1671 |
| 2018/0217583 A1* | 8/2018 | Samara | G05B 19/41855 |
| 2018/0231961 A1* | 8/2018 | Naito | B62D 65/18 |
| 2018/0290303 A1* | 10/2018 | Guerin | B25J 9/1664 |
| 2018/0307045 A1* | 10/2018 | Nishi | G02B 27/0172 |
| 2018/0326583 A1* | 11/2018 | Baroudi | B25J 9/1602 |
| 2018/0349829 A1* | 12/2018 | Peterson | G06Q 10/063112 |
| 2018/0350053 A1* | 12/2018 | Sugaya | G06T 7/001 |
| 2019/0011900 A1* | 1/2019 | Kobayashi | G05B 19/41865 |
| 2019/0047149 A1* | 2/2019 | Wouhaybi | B25J 9/163 |
| 2019/0061158 A1* | 2/2019 | Vu | G06T 17/10 |
| 2019/0088022 A1* | 3/2019 | Ochiai | G05B 19/41865 |
| 2019/0095854 A1* | 3/2019 | Pandya | G06Q 10/087 |
| 2019/0105779 A1* | 4/2019 | Einav | B25J 9/1676 |
| 2019/0121889 A1* | 4/2019 | Gold | G06F 16/2255 |
| 2019/0126482 A1* | 5/2019 | Tomita | B25J 9/1682 |
| 2019/0138973 A1* | 5/2019 | Akella | G06N 3/08 |
| 2019/0143517 A1* | 5/2019 | Yang | G06K 9/6271 |
| | | | 700/245 |
| 2019/0205657 A1* | 7/2019 | Ikeda | G06K 9/00342 |
| 2019/0270201 A1* | 9/2019 | Ding | B25J 9/1656 |
| 2019/0286113 A1* | 9/2019 | Halaby Senerman | |
| | | | G05B 19/4188 |
| 2019/0380239 A1* | 12/2019 | Kobayashi | G05B 19/41865 |
| 2019/0386929 A1* | 12/2019 | Nakazawa | G06F 9/5083 |
| 2019/0391184 A1* | 12/2019 | Adachi | G01R 19/00 |

FOREIGN PATENT DOCUMENTS

| | | |
|---|---|---|
| EP | 2626757 A1 | 8/2013 |
| WO | WO2012141601 | 10/2012 |
| WO | WO2017040167 | 3/2017 |

OTHER PUBLICATIONS

Matthew Zeiler & Rob Fergus, Visualizing and Understanding Convolution Networks, arXiv;1311.2901v3, Nov. 28, 2013, pp. 11.

Ross Girshick, First R-CNN, Proceedings of the 2015 IEEE International Conference on Computer Vision (ICCV), p. 1440-1448, Dec. 7-13, 2015.

Shaoqing Ren et al., Faster R-CNN Towards: Real Time Object Detection with Region Proposal Networks, Proceedings of the 28th International Conference on Neural Information Processing Systems, vol. 1, p. 91-99, Dec. 7-12, 2015.

Christian Szegedy et al., Inception-v4, Inception-Resnet and the Impact of Residual Connections on Learning, ICLR 2016 Workshop, Feb. 18, 2016.

Jonathan Huang et al., Speed/Accuracy Trade-Offs for Modern Convolutional Object Detectors, Proceedings of the 2017 IEEE Conference on Computer Vision and Pattern Recognition (CVPR), Nov. 9, 2017.

* cited by examiner

1400

Receiving one or more sensor streams with one or more engines
1402

Utilizing the engine(s) to identify one or more actions that are performed at a 1st station of a plurality of stations within the sensor stream(s)
1404

Utilizing the engine(s) to identify one or more actions that are performed at a 2nd station of the plurality of stations within the sensor stream(s)
1406

Storing in one or more data structures the received sensor stream(s), the identified one or more actions performed at the first station, and the identified one or more actions performed at the second station, the identified one or more actions performed at each of the first and second stations are mapped to the sensor stream(s)
1408

Utilizing the engine(s) to characterize each of the identified one or more actions performed at each of the first and second stations to produce determined characterizations thereof
1410

Based on one or more of the determined characterizations, automatically producing a recommendation to move at least one of the identified one or more actions performed at one of the stations to another station to reduce cycle time
1412

FIG. 14

SYSTEMS AND METHODS FOR LINE BALANCING

CROSS-REFERENCE TO RELATED APPLICATION

This application claims the benefit of U.S. Provisional Patent Application No. 62/581,541 filed Nov. 3, 2017, entitled "System and Method for Automated Process Identification and Validation," by Prasad Akella et al., which is hereby incorporated by reference.

BACKGROUND

It is noted that the Toyota Production System (TPS) has popularized single piece flow manufacturing to deliver higher quality and greater productivity. One of the many tenets is the requirement that a piece moves on a line from one station to another as it is incrementally and completely assembled. Another tenet is that the slowest station on a sequential line, the bottleneck station, determines the speed of the entire line. By balancing all stations on the line, TPS ensures that idle time is minimized across the line and, more importantly, takt time is met. It is noted that takt time can be defined as the maximum amount of time in which a product needs to be produced in order to meet customer demand. Additionally, when lines are balanced, the process can often be made to execute with fewer stations on a line—thereby saving floor space and costs.

Another concept in manufacturing (as well as other sectors with partially ordered sequential operations such as health care, retail, warehouses, etc.) is referred to as the lean process. Ensuring the line is balanced so there is no waste (including, especially, idle time) is a key tenet of the lean process. To determine non-value added and wasted time, industrial engineers typically observe floor activities using stopwatches to measure and calculate task-time and cycle-time at every station, to determine bottlenecks, and to manually recommend moving tasks to balance the line so it is running at or below takt times.

Depending upon the market demand, labor churn, equipment failure, ergonomics requirements, product churn, etc. the frequency of re-balancing the line can vary significantly. In some situations, for example, when the labor churn is high, the system will never stabilize and will, therefore, need to be re-balanced frequently. In other cases, when long runs of product are possible, re-balancing may not required after the line is initially set up.

The manual nature of this process leads to several deficiencies. First, the worker's behavior is changed since he/she knows that they are being measured. Second, the data is biased by the very nature of the measurement process (e.g., the morning shift worker being measured might be faster or slower than the night shift worker). And, third, the data is sparsely sampled: the industrial engineer does not have the tools to get measurements over several shifts and days. So, any line balancing and optimization that is done is, by its very nature, suboptimal.

SUMMARY

Various embodiments in accordance with the present disclosure can address the disadvantages described above.

A line balancing system in accordance with various embodiments of the present disclosure is able to continuously gather data (e.g., one or more streams of data) at all times that the line is running, including sampling one or more video streams at tens of frames per second, but is not limited to such. Further, a line balancing system in accordance with various embodiments is able to automatically break this data down into the underlying tasks. Therefore, a line balancing system in accordance with various embodiments is able to deliver time and motion data at a level of granularity never before possible. It is noted that a line balancing system in accordance with various embodiments can be implemented with one or more engines as described herein, but is not limited to such. Further, in various embodiments, the rebalancing can be done dynamically or over longer periods of time.

A line balancing system in accordance with various embodiments of the present disclosure directly benefits from one or more engines (e.g., described herein), which extracts action information and one or more finite state machine systems. The action information, depending on the sampling rate of the vision system (or one or more sensor systems), is accurate to sub-second. For example, accurate and detailed data points for thousands of repetitions of each action (or operation of the production process) are now available. The line balancing system can create statistical measures, from this large data set, for each action in the process.

Simultaneously (or at substantially the same time) in various embodiments, the one or more finite state machines of the line balancing system knows of process dependencies (e.g., within the production line). With the time and motion metrics and a knowledge of the process dependencies in hand, the line balancing system in accordance with various embodiments is able to propose one or more optimal real-locations of actions (or tasks or steps or operations) so the cycle time at every station is probabilistically (e.g., to some pre-determined confidence level) at or below the takt time for each action or task. It is noted that the line balancing system in accordance with various embodiments can optimize across all the stations on a line, globally or locally, sequentially or non-sequentially, off-line or in real-time, moving one or more actions or tasks to a different station of a production line than initially assigned. In addition, when done, each station is balanced and there is the distinct possibility, depending on how much waste there was in the original production line, of eliminating one or more stations of the production line.

Simultaneously (or at substantially the same time) in various embodiments, the one or more finite state machines of the line balancing system knows of process dependencies (e.g., within the production line). With the time and motion metrics and a knowledge of the process dependencies in hand, the line balancing system in accordance with various embodiments is able to propose one or more optimal designs for a new product introduction on an existing line. Additionally, the line balancing system can propose optimal designs for new lines which involve substantially the same sets of actions for which the system has collected data in the past.

In addition, in various embodiments, the line balancing system incorporates various constraints inherent to any sequential process or assembly line—certain tasks can only be performed in a certain order (for example a hard drive must be placed into the chassis before it can be affixed with screws), certain tasks can only be performed at certain stations because the equipment required for the tasks is fixed to certain stations, cost constraints having to do with labor, machine operation or materials costs as well as time and space constraints having to do with materials storage and delivery. In various embodiments, the line balancing system can incorporate some or all of these constraints into the solution process.

In addition, in various embodiments, a constrained optimization tool (e.g., linear programming, genetic algorithms, dynamic programming, branch and bound methods, etc.), heuristic approaches or simulation based approaches (e.g., Monte Carlo methods) can be used by a line balancing system to mathematically or programmatically determine a more optimal re-allocation of actions (or operations or tasks) to stations on the production line. Given that the data that the line balancing system is gathering reflects the variability in the process, the line balancing system incorporates information about the statistical nature of the data in the solution process.

In various embodiments, the statistical characteristics of the task data, especially the nature of the variability of the task performance times can involve a novel constrained optimization algorithm which utilizes a new framework to reflect these statistical characteristics. New mathematical techniques are combined with certain existing techniques listed above (in current or modified forms) to implement this framework to solve the line balancing problem.

In various embodiments, a method can include receiving one or more sensor streams with one or more engines. The one or more engines are utilized to identify one or more actions that are performed at a first station of a plurality of stations within the one or more sensor streams. In addition, the one or more engines are utilized to identify one or more actions that are performed at a second station of the plurality of stations within the one or more sensor streams. The received one or more sensor streams, the identified one or more actions performed at the first station, and the identified one or more actions performed at the second station are stored in one or more data structures. The identified one or more actions performed at each of the first and second stations are mapped to the one or more sensor streams. The one or more engines are utilized to characterize each of the identified one or more actions performed at each of the first and second stations to produce determined characterizations thereof. Based on one or more of the determined characterizations, automatically producing a recommendation to move at least one of the identified one or more actions performed at one of the stations to another station to reduce cycle time. In various embodiments, such a recommendation can be produced in real-time while the line is running or offline (or post-facto or on-demand) for later implementation. In various embodiments, such a recommendation can be produced either dynamically or post-facto, but is not limited to such.

In various embodiments, a system can include one or more sensors, one or more data storage units, and one or more engines coupled to the one or more sensors and the one or more data storage units. The one or more engines are configured to receive one or more sensor streams from the one or more sensors. In addition, the one or more engines are configured to identify one or more actions that are performed at a first station of a plurality of stations within the one or more sensor streams. The one or more engines are also configured to identify one or more actions that are performed at a second station of the plurality of stations within the one or more sensor streams. Furthermore, the one or more engines are configured to store the received one or more sensor streams, the identified one or more actions performed at the first station, and the identified one or more actions performed at the second station in one or more data structures on the one or more data storage units. Note that the identified one or more actions performed at each of the first and second stations are mapped to the one or more sensor streams. Moreover, the one or more engines are configured to characterize each of the identified one or more actions performed at each of the first and second stations to produce determined characterizations thereof. Additionally, based on one or more of the determined characterizations, the one or more engines are configured to automatically produce a recommendation to move at least one of the identified one or more actions performed at one of the stations to another station to reduce cycle time. In various embodiments, such a recommendation can be produced in real-time while the line is running or offline (or post-facto or on-demand) for later implementation. In various embodiments, such a recommendation can be produced either dynamically or post-facto, but is not limited to such.

In various embodiments, the system of the previous paragraph can further include a network configured to communicatively couple the one or more sensors, the one or more engines, and the one or more data storage units. In various embodiments, the system can further include a data compression unit communicatively coupled between the one or more sensors and the network. The data compression unit can be configured to compress the data of the one or more sensor streams before transmission across the network.

In various embodiments, one or more non-transitory computing device-readable storage mediums storing instructions executable by one or more engines to perform a method can include receiving one or more sensor streams with the one or more engines. Furthermore, the method can include utilizing the one or more engines to identify one or more actions that are performed at a first station of a plurality of stations of a production line within the one or more sensor streams. The method can also include utilizing the one or more engines to identify one or more actions that are performed at a second station of the plurality of stations of the production line within the one or more sensor streams. In addition, the method can include storing in one or more data structures the received one or more sensor streams, the identified one or more actions performed at the first station, and the identified one or more actions performed at the second station. It is noted that the identified one or more actions performed at each of the first and second stations are mapped to the one or more sensor streams. Moreover, the method can include utilizing the one or more engines to characterize each of the identified one or more actions performed at each of the first and second stations to produce determined characterizations thereof. Additionally, based on one or more of the determined characterizations, the method can include automatically producing a recommendation with the one or more engines to move at least one of the identified one or more actions performed at one of the stations to another station to reduce cycle time of the production line. In various embodiments, such a recommendation can be produced in real-time while the line is running or post-facto (or off-line or on-demand) for later implementation. In various embodiments, such a recommendation can be produced either dynamically or post-facto, but is not limited to such.

While various embodiments in accordance with the present disclosure have been specifically described within this Summary, it is noted that the claimed subject matter are not limited in any way by these various embodiments.

BRIEF DESCRIPTION OF THE DRAWINGS

Within the accompanying drawings, various embodiments in accordance with the present disclosure are illus

FIG. 14 is a flow chart of an exemplary method in accordance with various embodiments of the present disclosure.

DETAILED DESCRIPTION

As used herein the term process can include processes, procedures, transactions, routines, practices, and the like. As used herein the term sequence can include sequences, orders, arrangements, and the like. As used herein the term action can include actions, steps, tasks, activity, motion, movement, and the like. As used herein the term object can include objects, parts, components, items, elements, pieces, assemblies, sub-assemblies, and the like. As used herein a process can include a set of actions or one or more subsets of actions, arranged in one or more sequences, and performed on one or more objects by one or more actors. As used herein a cycle can include a set of processes or one or more subsets of processes performed in one or more sequences. As used herein a sensor stream can include a video sensor stream, thermal sensor stream, infrared sensor stream, hyperspectral sensor stream, audio sensor stream, depth data stream, and the like. As used herein frame based sensor stream can include any sensor stream that can be represented by a two or more dimensional array of data values. As used herein the term parameter can include parameters, attributes, or the like. As used herein the term indicator can include indicators, identifiers, labels, tags, states, attributes, values or the like. As used herein the term feedback can include feedback, commands, directions, alerts, alarms, instructions, orders, and the like. As used herein the term actor can include actors, workers, employees, operators, assemblers, contractors, associates, managers, users, entities, humans, cobots, robots, and the like as well as combinations of them. As used herein the term robot can include a machine, device, apparatus or the like, especially one programmable by a computer, capable of carrying out a series of actions automatically. The actions can be autonomous, semi-autonomous, assisted, or the like. As used herein the term cobot can include a robot intended to interact with humans in a shared workspace. As used herein the term package can include packages, packets, bundles, boxes, containers, cases, cartons, kits, and the like. As used herein, real time can include responses within a given latency, which can vary from sub-second to seconds.

Figure 1:
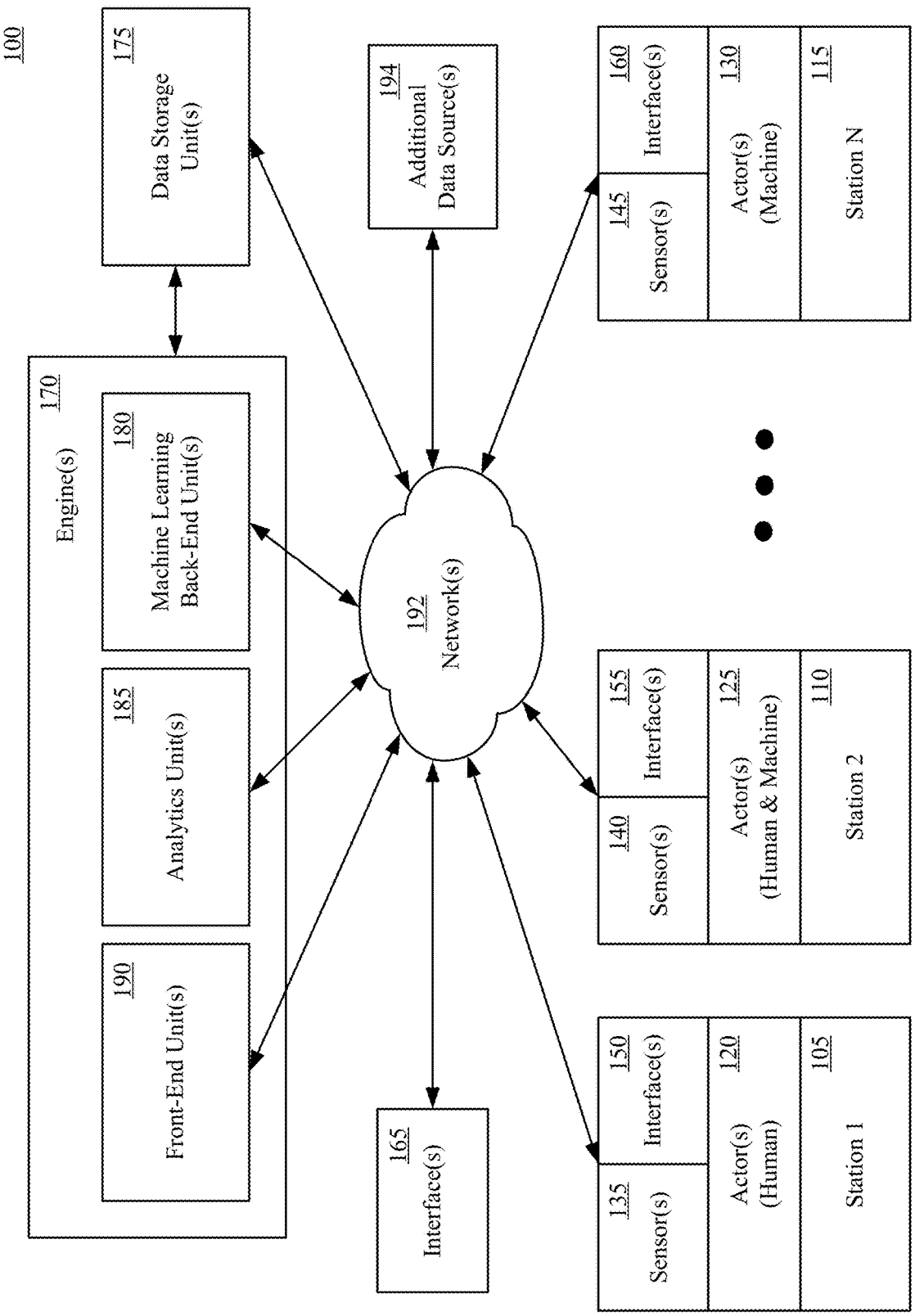
- FIG. 1 shows an action recognition and analytics system, in accordance with aspect of the present technology.

Referring to FIG. 1 an action recognition and analytics system, in accordance with aspect of the present technology, is shown. The action recognition and analytics system 100 can be deployed in a manufacturing, health care, warehousing, shipping, retail, restaurant or similar context. A manufacturing context, for example, can include one or more stations 105-115 and one or more actors 120-130 disposed at the one or more stations. The actors can include humans, machine or any combination therefore. For example, individual or multiple workers can be deployed at one or more stations along a manufacturing assembly line. One or more robots can be deployed at other stations. A combination of one or more workers and/or one or more robots can be deployed at additional stations. It is to be noted that the one or more stations 105-115 and the one or more actors are not generally considered to be included in the system 100.

In a health care implementation, an operating room can comprise a single station implementation. A plurality of sensors, such as video cameras, thermal imaging sensors, depth sensors, or the like, can be disposed non-intrusively at various positions around the operating room. One or more additional sensors, such as audio, temperature, acceleration, torque, compression, tension, or the like sensors, can also be disposed non-intrusively at various positions around the operating room.

In a shipping implementation, the plurality of stations may represent different loading docks, conveyor belts, forklifts, sorting stations, holding areas, and the like. A plurality of sensors, such as video cameras, thermal imaging sensors, depth sensors, or the like, can be disposed non-intrusively at various positions around the loading docks, conveyor belts, forklifts, sorting stations, holding areas, and the like. One or more additional sensors, such as audio, temperature, acceleration, torque, compression, tension, or the like sensors, can also be disposed non-intrusively at various positions.

In a retailing implementation, the plurality of stations may represent one or more loading docks, one or more stock rooms, the store shelves, the point of sale (e.g. cashier stands, self-checkout stands and auto-payment geofence), and the like. A plurality of sensors such as video cameras, thermal imaging sensors, depth sensors, or the like, can be disposed non-intrusively at various positions around the loading docks, stock rooms, store shelves, point of sale stands and the like. One or more additional sensors, such as audio, acceleration, torque, compression, tension, or the like sensors, can also be disposed non-intrusively at various positions around the loading docks, stock rooms, store shelves, point of sale stands and the like.

In a warehousing or online retailing implementation, the plurality of stations may represent receiving areas, inventory storage, picking totes, conveyors, packing areas, shipping areas, and the like. A plurality of sensors, such as video cameras, thermal imaging sensors, depth sensors, or the like, can be disposed non-intrusively at various positions around the receiving areas, inventory storage, picking totes, conveyors, packing areas, and shipping areas. One or more additional sensors, such as audio, temperature, acceleration, torque, compression, tension, or the like sensors, can also be disposed non-intrusively at various positions.

Aspect of the present technology will be herein further described with reference to a manufacturing context so as to best explain the principles of the present technology without obscuring aspects of the present technology. However, the present technology as further described below can also be readily applied in health care, warehousing, shipping, retail, restaurants, and numerous other similar contexts.

The action recognition and analytics system 100 can include one or more interfaces 135-165. The one or more interface 135-145 can include one or more sensors 135-145 disposed at the one or more stations 105-115 and configured to capture streams of data concerning cycles, processes, actions, sequences, object, parameters and or the like by the one or more actors 120-130 and or at the station 105-115. The one or more sensors 135-145 can be disposed non-intrusively, so that minimal to changes to the layout of the assembly line or the plant are required, at various positions around one or more of the stations 105-115. The same set of one or more sensors 135-145 can be disposed at each station 105-115, or different sets of one or more sensors 135-145 can be disposed at different stations 105-115. The sensors 135-145 can include one or more sensors such as video cameras, thermal imaging sensors, depth sensors, or the like. The one or more sensors 135-145 can also include one or more other sensors, such as audio, temperature, acceleration, torque, compression, tension, or the like sensors.

The one or more interfaces 135-165 can also include but not limited to one or more displays, touch screens, touch pads, keyboards, pointing devices, button, switches, control panels, actuators, indicator lights, speakers, Augmented Reality (AR) interfaces, Virtual Reality (VR) interfaces, desktop Personal Computers (PCs), laptop PCs, tablet PCs, smart phones, robot interfaces, cobot interfaces. The one or more interfaces 135-165 can be configured to receive inputs from one or more actors 120-130, one or more engines 170 or other entities. Similarly, the one or more interfaces 135-165 can be configured to output to one or more actors 120-130, one or more engine 170 or other entities. For example, the one or more front-end units 190 can output one or more graphical user interfaces to present training content, work charts, real time alerts, feedback and or the like on one or more interfaces 165, such displays at one or more stations 120-130, at management portals on tablet PCs, administrator portals as desktop PCs or the like. In another example, the one or more front-end units 190 can control an actuator to push a defective unit off the assembly line when a defect is detected. The one or more front-end units can also receive responses on a touch screen display device, keyboard, one or more buttons, microphone or the like from one or more actors. Accordingly, the interfaces 135-165 can implement an analysis interface, mentoring interface and or the like of the one or more front-end units 190.

The action recognition and analytics system 100 can also include one or more engines 170 and one or more data storage units 175. The one or more interfaces 135-165, the one or more data storage units 175, the one or more machine learning back-end units 180, the one or more analytics units 185, and the one or more front-end units 190 can be coupled together by one or more networks 192. It is also to be noted that although the above described elements are described as separate elements, one or more elements of the action recognition and analytics system 100 can be combined together or further broken into different elements.

The one or more engines 170 can include one or more machine learning back-end units 180, one or more analytics units 185, and one or more front-end units 190. The one or more data storage units 175, the one or more machine learning back-end units 180, the one or more analytics units 185, and the one or more analytics front-end units 190 can be implemented on a single computing device, a common set of computing devices, separate computing device, or different sets of computing devices that can be distributed across the globe inside and outside an enterprise. Aspects of the one or more machine learning back-end units 180, the one or more analytics units 185 and the one or more front-end units 190, and or other computing units of the action recognition and analytics system 100 can be implemented by one or more central processing units (CPU), one or more graphics processing units (GPU), one or more tensor processing units (TPU), one or more digital signal processors (DSP), one or more microcontrollers, one or more field programmable gate arrays and or the like, and any combination thereof. In addition, the one or more data storage units 175, the one or more machine learning back-end units 180, the one or more analytics units 185, and the one or more front-end units 190 can be implemented locally to the one or more stations 105-115, remotely from the one or more stations 105-115, or any combination of locally and remotely. In one example, the one or more data storage units 175, the one or more machine learning back-end units 180, the one or more analytics units 185, and the one or more front-end units 190 can be implemented on a server local (e.g., on site at the manufacturer) to the one or more stations 105-115. In another example, the one or more machine learning back-end units 135, the one or more storage units 140 and analytics front-end units 145 can be implemented on a cloud computing service remote from the one or more stations 105-115. In yet another example, the one or more data storage units 175 and the one or more machine learning back-end units 180 can be implemented remotely on a server of a vendor, and one or more data storage units 175 and the one or more front-end units 190 are implemented locally on a server or computer of the manufacturer. In other examples, the one or more sensors 135-145, the one or more machine learning back-end units 180, the one or more front-end unit 190, and other computing units of the action recognition and analytics system 100 can perform processing at the edge of the network 192 in an edge computing implementation. The above example of the deployment of one or more computing devices to implement the one or more interfaces 135-165, the one or more engines 170, the one or more data storage units 140 and one or more analytics front-end units 145, are just some of the many different configuration for implementing the one or more machine learning back-end units 135, one or more data storage units 140. Any number of computing devices, deployed locally, remotely, at the edge or the like can be utilized for implementing the one or more machine learning back-end units 135, the one or more data storage units 140, the one or more analytics front-end units 145 or other computing units.

The action recognition and analytics system 100 can also optionally include one or more data compression units associated with one or more of the interfaces 135-165. The data compression units can be configured to compress or decompress data transmitted between the one or more interface 135-165, and the one or more engines 170. Data compression, for example, can advantageously allow the sensor data from the one or more interface 135-165 to be transmitted across one or more existing networks 192 of a manufacturer. The data compression units can also be integral to one or more interfaces 135-165 or implemented separately. For example, video capture sensors may include an integral Motion Picture Expert Group (MPEG) compression unit (e.g., H-264 encoder/decoder). In an exemplary implementation, the one or more data compression units can use differential coding and arithmetic encoding to obtain a 20× reduction in the size of depth data from depth sensors. The data from a video capture sensor can comprise roughly 30 GB of H.264 compressed data per camera, per day for a factory operation with three eight-hour shifts. The depth data can comprise roughly another 400 GB of uncompressed data per sensor, per day. The depth data can be compressed by an algorithm to approximately 20 GB per sensor, per day. Together, a set of a video sensor and a depth sensor can generate approximately 50 GB of compressed data per day. The compression can allow the action recognition and analytics system 100 to use a factory's network 192 to move and store data locally or remotely (e.g., cloud storage).

The action recognition and analytics system 100 can also be communicatively coupled to additional data sources 194, such as but not limited to a Manufacturing Execution Systems (MES), warehouse management system, or patient management system. The action recognition and analytics system 100 can receive additional data, including one or more additional sensor streams, from the additional data sources 194. The action recognition and analytics system 100 can also output data, sensor streams, analytics result and or the like to the additional data sources 194. For example, the action recognition can identify a barcode on an object and provide the barcode input to a MES for tracking.

The action recognition and analytics system 100 can continually measure aspects of the real-world, making it possible to describe a context utilizing vastly more detailed data sets, and to solve important business problems like line balancing, ergonomics, and or the like. The data can also reflect variations over time. The one or more machine learning back-end units 170 can be configured to recognize, in real time, one or more cycles, processes, actions, sequences, objects, parameters and the like in the sensor streams received from the plurality of sensors 135-145. The one or more machine learning back-end units 180 can recognize cycles, processes, actions, sequences, objects, parameters and the like in sensor streams utilizing deep learning, decision tree learning, inductive logic programming, clustering, reinforcement learning, Bayesian networks, and or the like.

Figure 2:
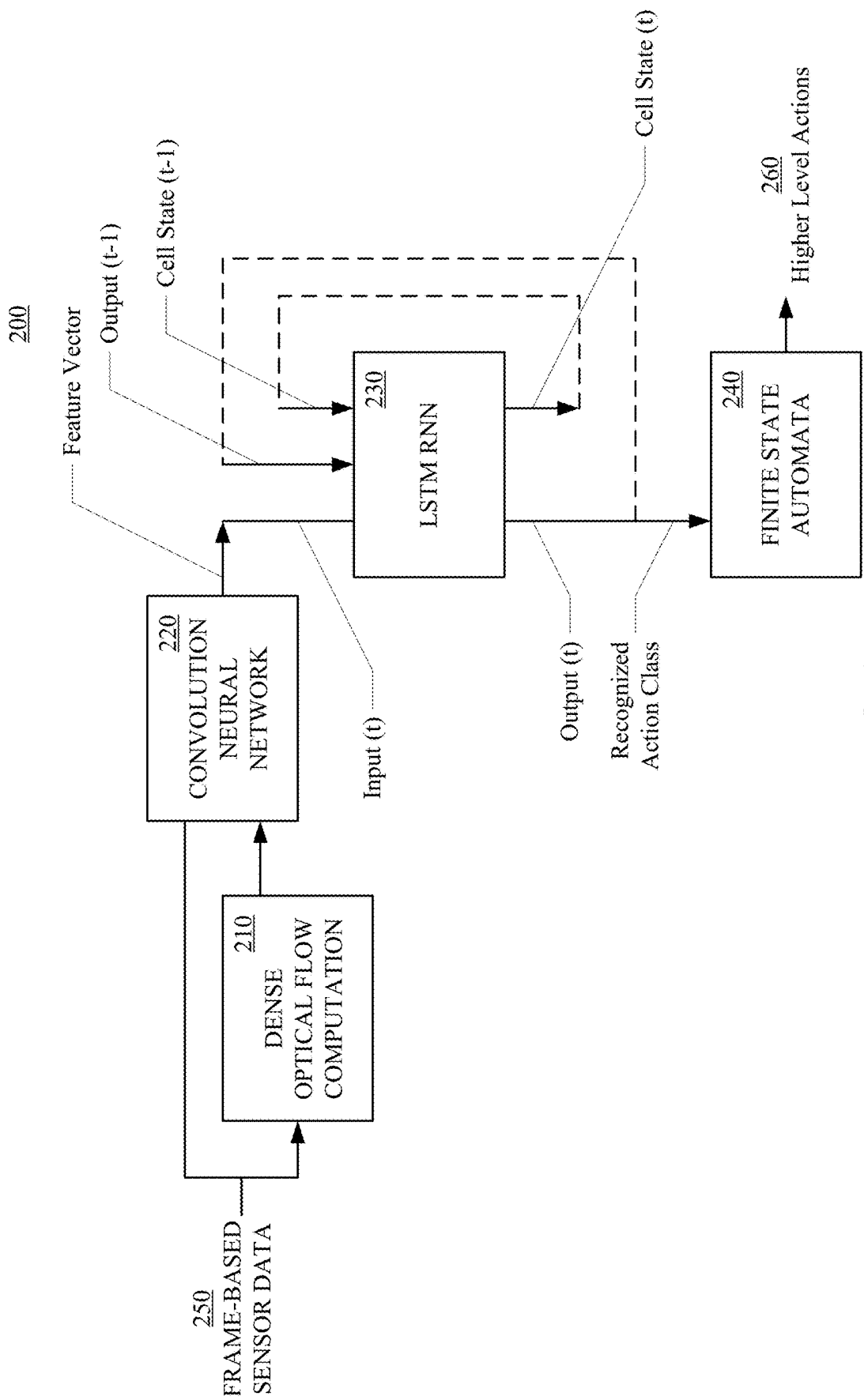
FIG. 2 shows an exemplary deep learning type machine learning back-end unit, in accordance with aspects of the present technology.

Referring now to FIG. 2, an exemplary deep learning type machine learning back-end unit, in accordance with aspects of the present technology, is shown. The deep learning unit 200 can be configured to recognize, in real time, one or more cycles, processes, actions, sequences, objects, parameters and the like in the sensor streams received from the plurality of sensors 120-130. The deep learning unit 200 can include a dense optical flow computation unit 210, a Convolution Neural Networks (CNNs) 220, a Long Short Term Memory (LSTM) Recurrent Neural Network (RNN) 230, and a Finite State Automata (FSA) 240. The CNNs 220 can be based on two-dimensional (2D) or three-dimensional (3D) convolutions. The dense optical flow computation unit 210 can be configured to receive a stream of frame-based sensor data 250 from sensors 120-130. The dense optical flow computation unit 210 can be configured to estimate an optical flow, which is a two-dimension (2D) vector field where each vector is a displacement vector showing the movement of points from a first frame to a second frame. The CNNs 220 can receive the stream of frame-based sensor data 250 and the optical flow estimated by the dense optical flow computation unit 210. The CNNs 220 can be applied to video frames to create a digest of the frames. The digest of the frames can also be referred to as the embedding vector. The digest retains those aspects of the frame that help in identifying actions, such as the core visual clues that are common to instances of the action in question.

In a three-dimensional Convolution Neural Network (3D CNN) based approach, spatio-temporal convolutions can be performed to digest multiple video frames together to recognize actions. For 3D CNN, the first two dimension can be along space, and in particular the width and height of each video frame. The third dimension can be along time. The neural network can learn to recognize actions not just from the spatial pattern in individual frame, but also jointly in space and time. The neural network is not just using color patterns in one frame to recognize actions. Instead, the neural network is using how the pattern shifts with time (i.e., motion cues) to come up with its classification. According the 3D CNN is attention driven, in that it proceeds by identifying 3D spatio-temporal bounding boxes as Regions of Interest (RoI) and focusses on them to classify actions.

In one implementation, the input to the deep learning unit 200 can include multiple data streams. In one instance, a video sensor signal, which includes red, green and blue data streams, can comprise three channels. Depth image data can comprise another channel. Additional channels can accrue from temperature, sound, vibration, data from sensors (e.g., torque from a screwdriver) and the like. From the RGB and depth streams, dense optical flow fields can be computed by the dense optical flow computation unit 210 and fed to the Convolution Neural Networks (CNNs) 220. The RGB and depth streams can also be fed to the CNNs 220 as additional streams of derived data.

The Long Short Term Memory (LSTM) Recurrent Neural Network (RNN) 230 can be fed the digests from the output of the Convolution Neural Networks (CNNs) 220. The LSTM can essentially be a sequence identifier that is trained to recognize temporal sequences of sub-events that constitute an action. The combination of the CNNs and LSTM can be jointly trained, with full back-propagation, to recognize low-level actions. The low-level actions can be referred to as atomic actions, like picking a screw, picking a screwdriver, attaching screw to screwdriver and the like. The Finite State Automata (FSA) 240 can be mathematical models of computations that include a set of state and a set of rules that govern the transition between the states based on the provided input. The FSA 240 can be configured to recognize higher-level actions 260 from the atomic actions. The high-level actions 260 can be referred to as molecular actions, for example turning a screw to affix a hard drive to a computer chassis. The CNNs and LSTM can be configured to perform supervised training on the data from the multiple sensor streams. In one implementation, approximately 12 hours of data, collected over the course of several days, can be utilized to train the CNNs and LSTM combination.

Figure 3:
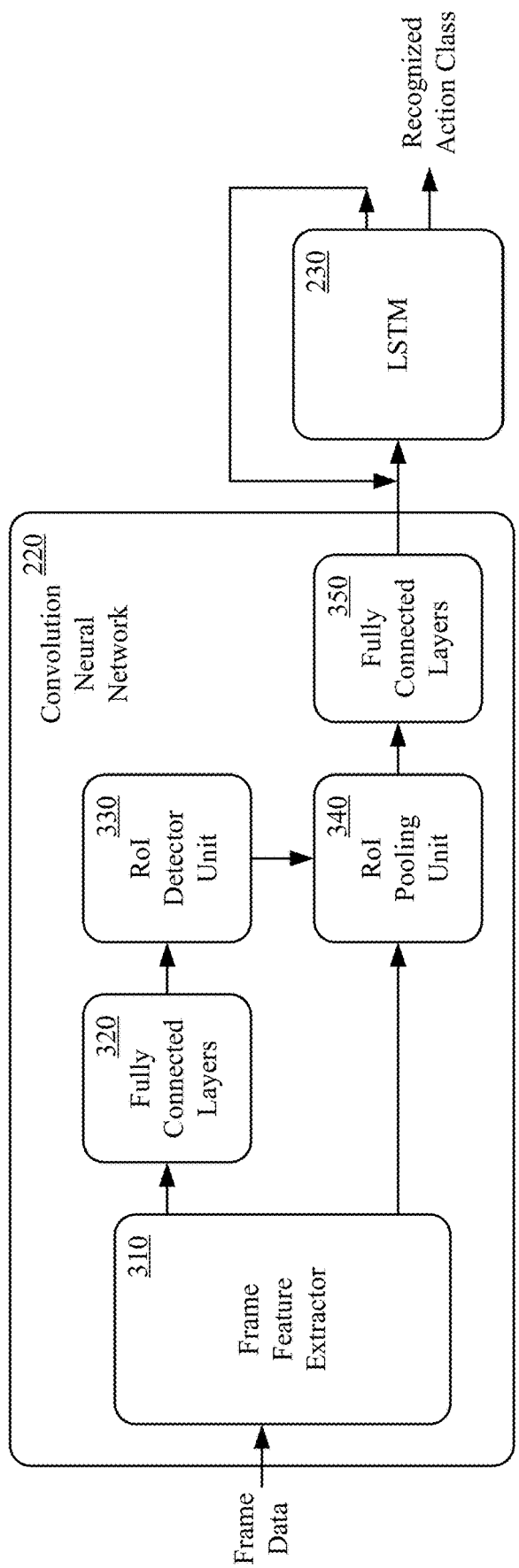
FIG. 3 shows an exemplary Convolution Neural Networks (CNNs) and Long Short Term Memory (LSTM) Recurrent Neural Network (RNN), in accordance with aspects of the present technology.
Figure 4:
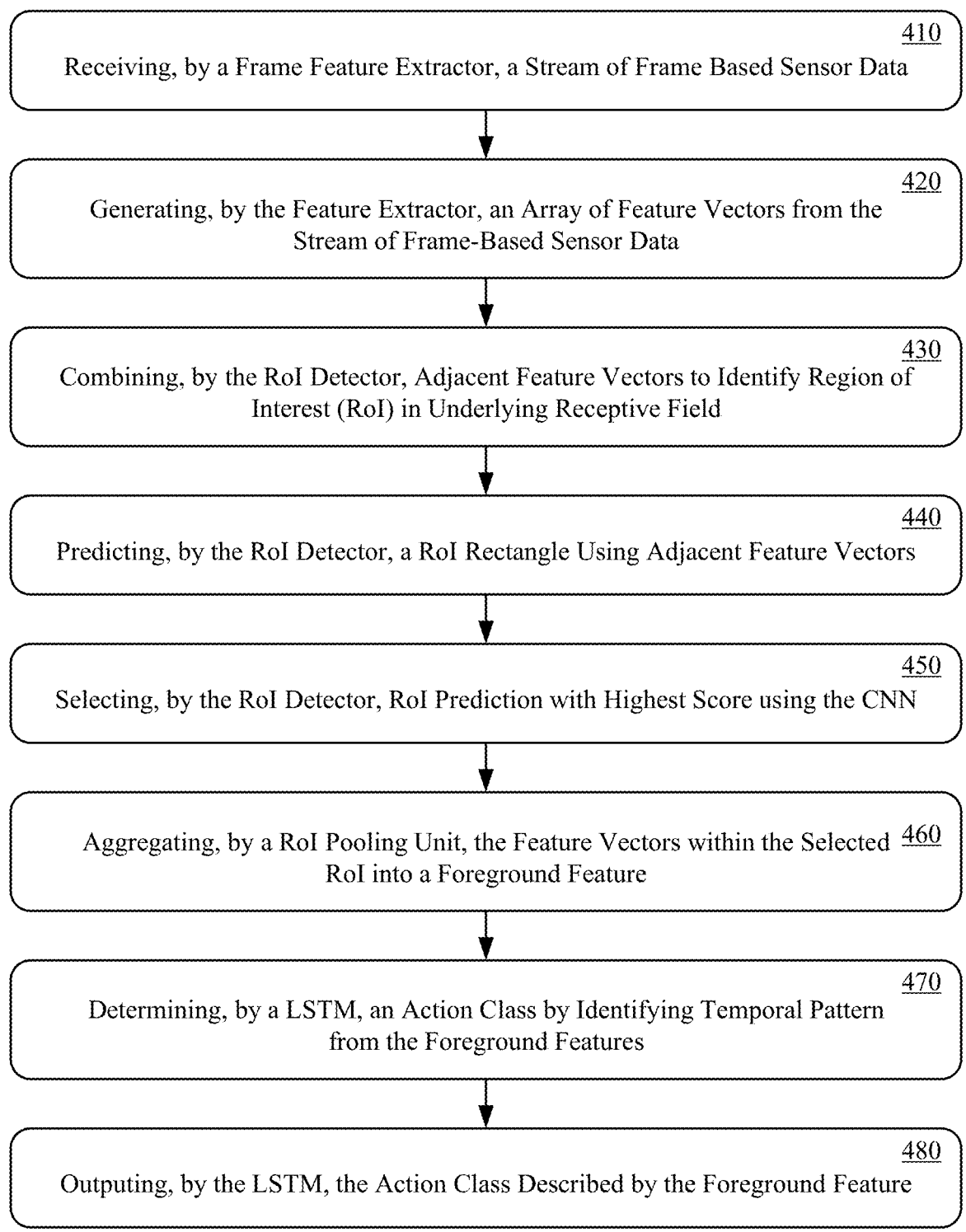
FIG. 4 shows an exemplary method of detecting actions in a sensor stream, in accordance with aspects of the present technology.

Referring now to FIG. 3, an exemplary Convolution Neural Networks (CNNs) and Long Short Term Memory (LSTM) Recurrent Neural Network (RNN), in accordance with aspects of the present technology, is shown. The CNNs can include a frame feature extractor 310, a first Fully Connected (FC) layer 320, a Region of Interest (RoI) detector unit 330, a RoI pooling unit 340, and a second Fully Connected (FC) layer 350. The operation of the CNNs and LSTM will be further explained with reference to FIG. 4, which shows an exemplary method of detecting actions in a sensor stream.

The frame feature extractor 310 of the Convolution Neural Networks (CNNs) 220 can receive a stream of frame-based sensor data, at 410. At 420, the frame feature extractor 310 can perform a two-dimensional convolution operation on the received video frame and generate a two-dimensional array of feature vectors. The frame feature extractor 310 can work on the full resolution image, wherein a deep network is effectively sliding across the image generating a feature vector at each stride position. Thus, each element of the 2D feature vector array is a descriptor for the corresponding receptive field (e.g., fixed portion of the underlying image). The first Fully Connected (FC) layer can flatten the high-level features extracted by the frame feature extractor 310, and provide additional non-linearity and expressive power, enabling the machine to learn complex non-linear combinations of these features.

At 430, the RoI detector unit 330 can combine neighboring feature vectors to make a decision on whether the underlying receptive field belongs to a Region of Interest (RoI) or not. If the underlying receptive field belongs to a RoI, a RoI rectangle can be predicted from the same set of neighboring feature vectors, at 440. At, 450, a RoI rectangle with a highest score can be chosen by the RoI detector unit 330. For the chosen RoI rectangle, the feature vectors lying within it can be aggregated by the RoI pooling unit 340, at 460. The aggregated feature vector is a digest/descriptor for the foreground for that video frame.

In one implementation, the RoI detector unit 330 can determine a static RoI. The static RoI identifies a Region of Interest (RoI) within an aggregate set of feature vectors describing a video frame, and generates a RoI area for the identified RoI. A RoI area within a video frame can be indicated with a RoI rectangle that encompasses an area of the video frame designated for action recognition, such as an area in which actions are performed in a process. Alternatively, the RoI area can be designated with a box, circle, highlighted screen, or any other geometric shape or indicator having various scales and aspect ratios used to encompass a RoI. The area within the RoI rectangle is the area within the video frame to be processed by the Long Short Term Memory (LSTM) for action recognition.

The Long Short Term Memory (LSTM) can be trained using a RoI rectangle that provides, both, adequate spatial context within the video frame to recognize actions and independence from irrelevant portions of the video frame in the background. The trade-off between spatial context and background independence ensures that the static RoI detector can provide clues for the action recognition while avoiding spurious unreliable signals within a given video frame.

In another implementation, the RoI detector unit 330 can determine a dynamic RoI. A RoI rectangle can encompass areas within a video frame in which an action is occurring. By focusing on areas in which action occurs, the dynamic RoI detector enables recognition of actions outside of a static RoI rectangle while relying on a smaller spatial context, or local context, than that used to recognize actions in a static RoI rectangle.

In one implementation, the RoI pooling unit 340 extracts a fixed-sized feature vector from the area within an identified RoI rectangle, and discards the remaining feature vectors of the input video frame. The fixed-sized feature vector, or foreground feature, includes the feature vectors generated by the video frame feature extractor that are located within the coordinates indicating a RoI rectangle as determined by the RoI detector unit 330. Because the RoI pooling unit 340 discards feature vectors not included within the RoI rectangle, the Convolution Neural Networks (CNNs) 220 analyzes actions within the RoI only, thus ensuring that unexpected changes in the background of a video frame are not erroneously analyzed for action recognition.

In one implementation, the Convolution Neural Networks (CNNs) 220 can be an Inception ResNet. The Inception ResNet can utilize a sliding window style operation. Successive convolution layers output a feature vector at each point of a two-dimensional grid. The feature vector at location (x,y) at level l can be derived by weighted averaging features from a small local neighborhood (aka receptive field) N around the (x,y) at level l−1 followed by a pointwise non-linear operator. The non-linear operator can be the RELU (max(0,x)) operator.

In the sliding window, there can be many more than 7×7 points at the output of the last convolution layer. A Fully Connected (FC) convolution can be taken over the feature vectors from the 7×7 neighborhoods, which is nothing but applying one more convolution. The corresponding output represents the Convolution Neural Networks (CNNs) output at the matching 224×224 receptive field on the input image. This is fundamentally equivalent to applying the CNNs to each sliding window stop. However, no computation is repeated, thus keeping the inferencing computation cost real time on Graphics Processing Unit (GPU) based machines.

The convolution layers can be shared between RoI detector 330 and the video frame feature extractor 310. The RoI detector unit 330 can identify the class independent rectangular region of interest from the video frame. The video frame feature extractor can digest the video frame into feature vectors. The sharing of the convolution layers improves efficiency, wherein these expensive layers can be run once per frame and the results saved and reused.

One of the outputs of the Convolution Neural Networks (CNNs) is the static rectangular Region of Interest (RoI). The term "static" as used herein denotes that the RoI does not vary greatly from frame to frame, except when a scene change occurs, and it is also independent of the output class.

A set of concentric anchor boxes can be employed at each sliding window stop. In one implementation, there can be nine anchor boxes per sliding window stop for combinations of 3 scales and 3 aspect ratios. Therefore, at each sliding window stop there are two set of outputs. The first set of outputs can be a Region of Interest (RoI) present/absent that includes 18 outputs of the form 0 or 1. An output of 0 indicates the absence of a RoI within the anchor box, and an output of 1 indicates the presence of a RoI within the anchor box. The second set of outputs can include Bounding Box (BBox) coordinates including 36 floating point outputs indicating the actual BBox for each of the 9 anchor boxes. The BBox coordinates are to be ignored if the RoI present/absent output indicates the absence of a RoI.

For training, sets of video frames with a per-frame Region of Interest (RoI) rectangle are presented to the network. In frames without a RoI rectangle, a dummy 0×0 rectangle can be presented. The Ground Truth for individual anchor boxes can be created via the Intersection over Union (IoU) of rectangles. For the $i_{th}$ anchor box $\vec{b_i}=\{x_i, y_i, w_i, h_i\}$ the derived Ground Truth for the RoI presence probability can be determined by Equation 1:

$$p_i^* = \begin{cases} 1 & IoU(\vec{b_i}, \vec{g}) >= 0.7 \\ 0 & IoU(\vec{b_i}, \vec{g}) <= 0.7 \\ \text{box unused for training} \end{cases}$$

where $\vec{g}=\{x_g, y_g, w_g, h_g\}$ is the Ground Truth RoI box for the entire frame.

The loss function can be determined by Equation 2:

$$L(p_i, p_i^*, \vec{b_i}, \vec{g}) = \sum_i \{-p_i^* \log\{p_i(S(x_i - x_g) + S(y_i - y_g) + S(w_i - w_g) + S(h_i - h_g))\}$$

where $p_i$ is the predicted probability for presence of Region of Interest (RoI) in the $i_{th}$ anchor box and the smooth loss function can be defined by Equation 3:

$$S(x) = \begin{cases} 0.5x^2 & |x| < 1 \\ |x| - 0.5 & \text{otherwise} \end{cases}$$

The left term in the loss function is the error in predicting the probability of the presence of a RoI, while the second term is the mismatch in the predicted Bounding Box (BBox). It should be noted that the second term vanishes when the ground truth indicates that there is no RoI in the anchor box.

The static Region of Interest (RoI) is independent of the action class. In another implementation, a dynamic Region of Interest (RoI), that is class dependent, is proposed by the CNNs. This takes the form of a rectangle enclosing the part of the image where the specific action is occurring. This increases the focus of the network and takes it a step closer to a local context-based action recognition.

Once a Region of Interest (RoI) has been identified, the frame feature can be extracted from within the RoI. These will yield a background independent frame digest. But this feature vector also needs to be a fixed size so that it can be fed into the Long Short Term Memory (LSTM). The fixed size can be achieved via RoI pooling. For RoI pooling, the RoI can be tiled up into 7×7 boxes. The mean of all feature vectors within a tile can then be determined. Thus, 49 feature vectors that are concatenated from the frame digest can be produced. The second Fully Connected (FC) layer 350 can provide additional non-linearity and expressive power to the machine, creating a fixed size frame digest that can be consumed by the LSTM 230.

At 470, successive foreground features can be fed into the Long Short Term Memory (LSTM) 230 to learn the temporal pattern. The LSTM 230 can be configured to recognize patterns in an input sequence. In video action recognition, there could be patterns within sequences of frames belonging to a single action, referred to as intra action patterns. There could also be patterns within sequences of actions, referred to as inter action patterns. The LSTM can be configured to learn both of these patterns, jointly referred to as temporal patterns. The Long Short Term Memory (LSTM) analyzes a series of foreground features to recognize actions belonging to an overall sequence. In one implementation, the LSTM outputs an action class describing a recognized action associated with an overall process for each input it receives. In another implementation, each class action is comprised of sets of actions describing actions associated with completing an overall process. Each action within the set of actions can be assigned a score indicating a likelihood that the action matches the action captured in the input video frame. Each action may be assigned a score such that the action with the highest score is designated the recognized action class.

Foreground features from successive frames can be feed into the Long Short Term Memory (LSTM). The foreground feature refers to the aggregated feature vectors from within the Region of Interest (RoI) rectangles. The output of the LSTM at each time step is the recognized action class. The loss for each individual frame is the cross entropy softmax loss over the set of possible action classes. A batch is defined as a set of three randomly selected set of twelve frame sequences in the video stream. The loss for a batch is defined as the frame loss averaged over the frame in the batch. The numbers twelve and three are chose empirically. The overall LSTM loss function is given by Equation 4:

$$L(B_1\{S_1, S_2, \ldots, S_{\|B\|}\}) = \sum_{k=1}^{\|B\|} \sum_{t=1}^{\|S_k\|} \sum_{i=1}^{\|A\|} \Box - \left(\frac{e^{a_{t_i}}}{\sum_{j=1}^{\|A\|} e^{a_{t_{ij}}}}\right) \log a_{t_i}^*$$

where B denotes a batch of $\|B\|$ frame sequences $\{S_1, S_2, \ldots, S_{\|B\|}\}$. $S_k$ comprises a sequence of $\|S_k\|$ frames, wherein in the present implementation $\|B\|=3$ and $\|S_k\|=12$ k. A denotes the set of all action classes, $\alpha_{t_i}$ denotes the $i_{th}$ action class score for the $t_{th}$ frame from LSTM and a denotes the corresponding Ground Truth.

Referring again to FIG. 1, the machine learning back-end unit 135 can utilize custom labelling tools with interfaces optimized for labeling RoI, cycles and action. The labelling tools can include both standalone application built on top of Open source Computer Vision (OpenCV) and web browser application that allow for the labeling of video segment.

Figure 5:
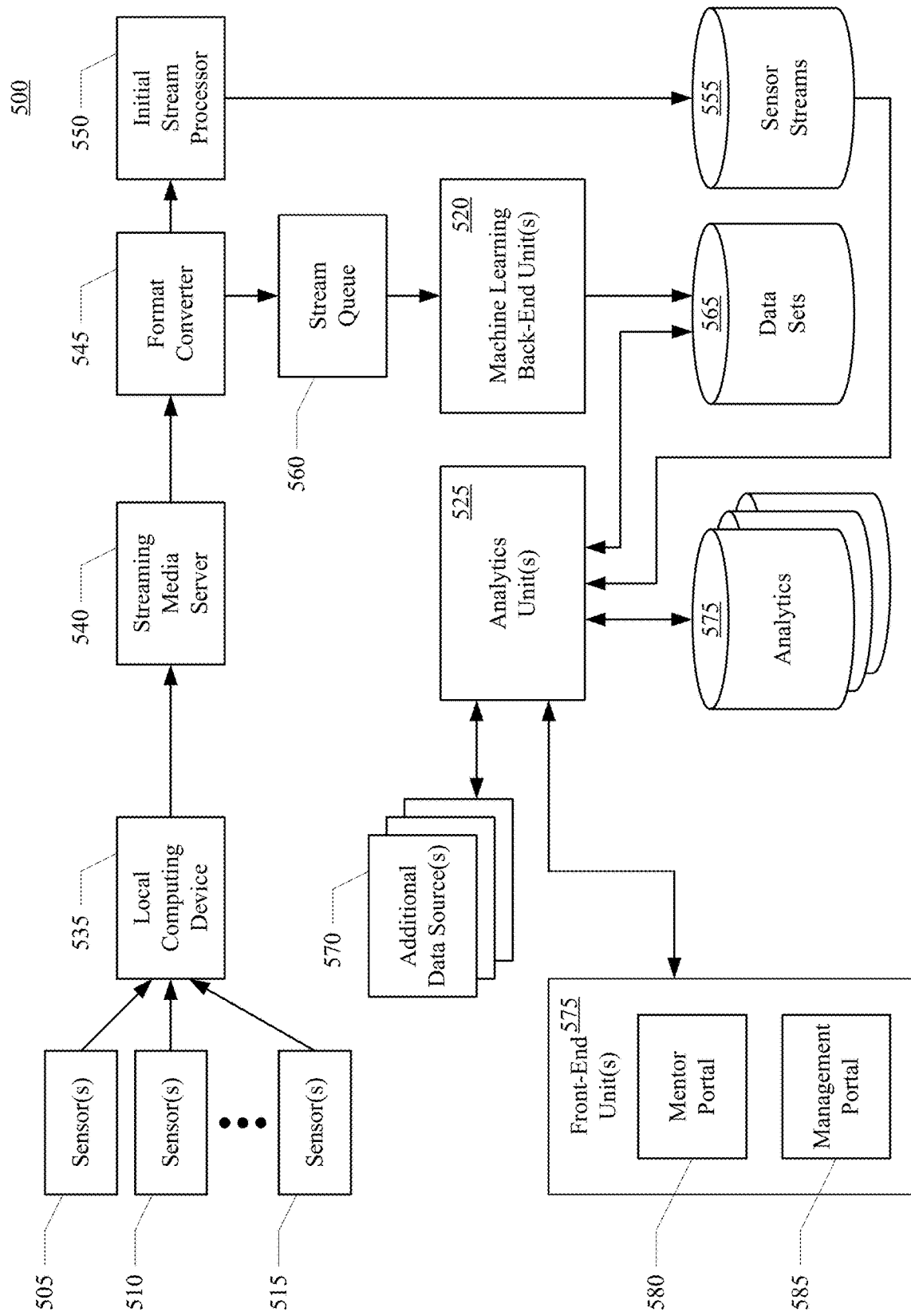
FIG. 5 shows an action recognition and analytics system, in accordance with aspect of the present technology.

Referring now to FIG. 5, an action recognition and analytics system, in accordance with aspect of the present technology, is shown. Again, the action recognition and analytics system 500 can be deployed in a manufacturing, health care, warehousing, shipping, retail, restaurant, or similar context. The system 500 similarly includes one or more sensors 505-515 disposed at one or more stations, one or more machine learning back-end units 520, one or more analytics units 525, and one or more front-end units 530. The one or more sensors 505-515 can be coupled to one or more local computing devices 535 configured to aggregate the sensor data streams from the one or more sensors 505-515 for transmission across one or more communication links to a streaming media server 540. The streaming media server 540 can be configured to received one or more streams of sensor data from the one or more sensors 505-515. A format converter 545 can be coupled to the streaming media server 540 to receive the one or more sensor data streams and convert the sensor data from one format to another. For example, the one or more sensors may generate Motion Picture Expert Group (MPEG) formatted (e.g., H.264) video sensor data, and the format converter 545 can be configured to extract frames of JPEG sensor data. An initial stream processor 550 can be coupled to the format convert 555. The initial stream processor 550 can be configured to segment the sensor data into pre-determined chucks, subdivide the chunks into key frame aligned segment, and create per segment sensor data in one or more formats. For example, the initial stream processor 550 can divide the sensor data into five minute chunks, subdivide the chunks into key frame aligned segment, and convert the key frame aligned segments into MPEG, MPEG Dynamic Adaptive Streaming over Hypertext Transfer Protocol (DASH) format, and or the like. The initial stream processor 550 can be configured to store the sensor stream segments in one or more data structures for storing sensor streams 555. In one implementation, as sensor stream segments are received, each new segment can be appended to the previous sensor stream segments stored in the one or more data structures for storing sensor streams 555.

Figure 6:
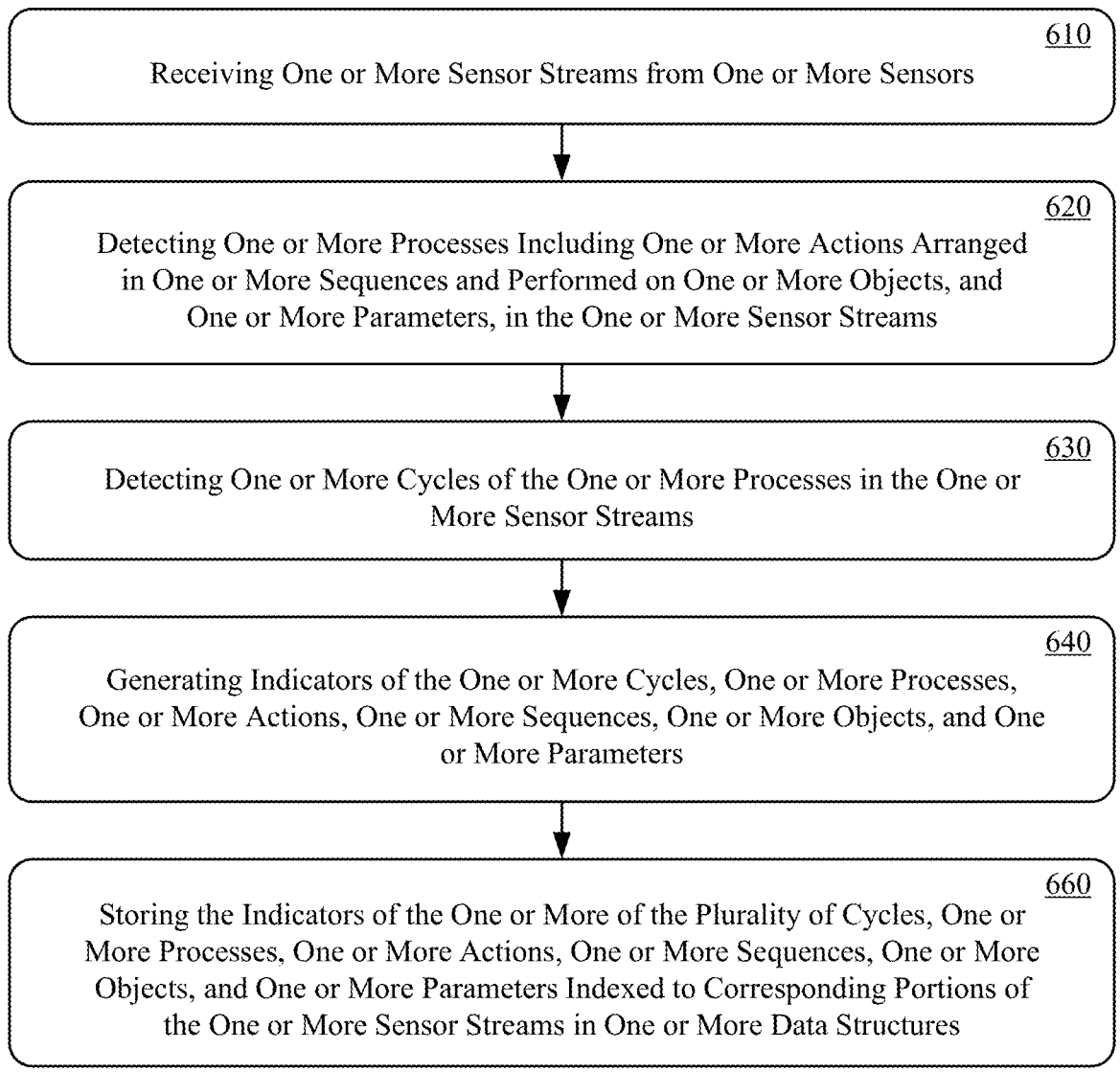
FIG. 6 shows an exemplary method of detecting actions, in accordance with aspects of the present technology.

A stream queue 560 can also be coupled to the format converter 545. The stream queue 560 can be configured to buffer the sensor data from the format converter 545 for processing by the one or more machine learning back-end units 520. The one or more machine learning back-end units 520 can be configured to recognize, in real time, one or more cycles, processes, actions, sequences, objects, parameters and the like in the sensor streams received from the plurality of sensors 505-515. Referring now to FIG. 6, an exemplary method of detecting actions, in accordance with aspects of the present technology, is shown. The action recognition method can include receiving one or more sensor streams from one or more sensors, at 610. In one implementation, one or more machine learning back-end units 520 can be configured to receive sensor streams from sensors 505-515 disposed at one or more stations.

At 620, a plurality of processes including one or more actions arranged in one or more sequences and performed on one or more objects, and one or more parameters can be detected. in the one or more sensor streams. At 630, one or more cycles of the plurality of processes in the sensor stream can also be determined. In one implementation, the one or more machine learning back-end units 520 can recognize cycles, processes, actions, sequences, objects, parameters and the like in sensor streams utilizing deep learning, decision tree learning, inductive logic programming, clustering, reinforcement learning, Bayesian networks, and or the like.

At 640, indicators of the one or more cycles, one or more processes, one or more actions, one or more sequences, one or more objects, and one or more parameters can be generated. In one implementation, the one or more machine learning back-end units 520 can be configured to generate indicators of the one or more cycles, processes, actions, sequences, objects, parameters and or the like. The indicators can include descriptions, identifiers, values and or the like associated with the cycles, processes, actions, sequences, objects, and or parameters. The parameters can include, but is not limited to, time, duration, location (e.g., x, y, z, t), reach point, motion path, grid point, quantity, sensor identifier, station identifier, and bar codes.

At 650, the indicators of the one or more cycles, one or more processes, one or more actions, one or more sequences, one or more objects, and one or more parameters indexed to corresponding portions of the sensor streams can be stored in one or more data structures for storing data sets 565. In one implementation, the one or more machine learning back-end units 520 can be configured to store a data set including the indicators of the one or more processes, one or more actions, one or more sequences, one or more objects, and one or more parameters for each cycle. The data sets can be stored in one or more data structures for storing the data sets 565. The indicators of the one or more cycles, one or more processes, one or more actions, one or more sequences, one or more objects, and one or more parameters in the data sets can be indexed to corresponding portion of the sensor streams in one or more data structures for storing sensor streams 555.

In one implementation, the one or more streams of sensor data and the indicators of the one or more of the plurality of cycles, one or more processes, one or more actions, one or more sequences, one or more objects and one or more parameters indexed to corresponding portions of the one or more streams of sensor data can be encrypted when stored to protect the integrity of the streams of sensor data and or the data sets. In one implementation, the one or more streams of sensor data and the indicators of the one or more of the plurality of cycles, one or more processes, one or more actions, one or more sequences, one or more objects and one or more parameters indexed to corresponding portions of the one or more streams of sensor data can be stored utilizing block chaining. The blockchaining can be applied across the cycles, sensor streams, stations, supply chain and or the like. The blockchaining can include calculating a cryptographic hash based on blocks of the data sets and or blocks of the streams of sensor data. The data sets, streams of sensor data and the cryptographic hash can be stored in one or more data structures in a distributed network.

Referring again to FIG. 5, the one or more analytics units 525 can be coupled to the one or more data structures for storing the sensor streams 555, one or more data structures for storing the data set 565, one or more additional sources of data 570, one or more data structures for storing analytics 575. The one or more analytics units 525 can be configured to perform statistical analysis on the cycle, process, action, sequence, object and parameter data in one or more data sets. The one or more analytics units 525 can also utilize additional data received from one or more additional data sources 570. The additional data sources 570 can include, but are not limited to, Manufacturing Execution Systems (MES), warehouse management system, or patient management system, accounting systems, robot datasheets, human resource records, bill of materials, and sales systems. Some examples of data that can be received from the additional data sources 570 can include, but is not limited to, time, date, shift, day of week, plant, factory, assembly line, sub-assembly line, building, room, supplier, work space, action capability, and energy consumption, ownership cost. The one or more analytics units 525 can be configured to utilize the additional data from one or more additional source of data 570 to update, correct, extend, augment or the like, the data about the cycles, processes, action, sequences, objects and parameters in the data sets. Similarly, the additional data can also be utilized to update, correct, extend, augment or the like, the analytics generate by the one or more analytics front-end units 525. The one or more analytics units 525 can also store trends and other comparative analytics utilizing the data sets and or the additional data, can use sensor fusion to merge data from multiple sensors, and other similar processing and store the results in the one or more data structures for storing analytics 575. In one implementation, one or more engines 170, such as the one or more machine learning back-end units 520 and or the one or more analytics units 525, can create a data structure including a plurality of data sets, the data sets including one or more indicators of at least one of one or more cycles, one or more processes, one or more actions, one or more sequences, one or more object and one or more parameters. The one or more engine 170 can build the data structure based on the one of one or more cycles, one or more processes, one or more actions, one or more sequences, one or more object and one or more parameters detected in the one or more sensor streams. The data structure definition, configuration and population can be performed in real time based upon the content of the one or more sensor streams. For example, Table 1 shows a table defined, configured and populated as the sensor streams are processed by the one or more machine learning back-end unit 520.

TABLE 1

ENTITY ID DATA STUCTURE (TABLE 1)

| FRAME | HUMAN | HAND | ARM | LEG | MOTHER-BOARD | SCREW |
|---|---|---|---|---|---|---|
| 1 | Yes | Yes | Yes | Yes | YES | Yes |
| 2 | Yes | No | No | Yes | Yes | No |
| 3 | Yes | Yes | Yes | Yes | YES | Yes |

The data structure creation process can continue to expand upon the initial structure and or create additional data structures base upon additional processing of the one or more sensor streams.

In one embodiment, the status associated with entities is added to a data structure configuration (e.g., engaged in an action, subject to a force, etc.) based upon processing of the access information. In one embodiment, activity associated with the entities is added to a data structure configuration (e.g., engaged in an action, subject to a force, etc.) based upon processing of the access information. One example of entity status data set created from processing of above entity ID data set (e.g., motion vector analysis of image object, etc.) is illustrated in Table 2.

TABLE 2

ENTITY STATUS DATA STRUCTURE (TABLE 2)

| FRAME | HAND MOVING | ARM MOVING | LEG MOVING | HUMAN MOVING |
|---|---|---|---|---|
| 1 | Yes | Yes | No | Yes |
| 2 | No | No | Yes | No |
| 3 | Yes | Yes | Yes | Yes |

In one embodiment, a third-party data structure as illustrated in Table 3 can be accessed.

TABLE 3

OSHA DATA STRUCTURE (TABLE 3)

| ACTIVITY | SAFE TO MOVE LEG | SAFE TO MOVE HAND |
|---|---|---|
| SCREWING TO MOTHERBOARD | No | Yes |
| LIFTING HOUSING | Yes | Yes |

In one embodiment, activity associated with entities is added to a data structure configuration (e.g., engaged in an action, subject to a force, etc.) based upon processing of the access information as illustrated in Table 4.

TABLE 4

ACTIVITY DATA STRUCTURE (TABLE 4)

| FRAME | SCREWING TO MOTHER-BOARD | HUMAN ACTION SAFE | MOTHER-BOARD COMPLETE |
|---|---|---|---|
| 1 | Yes | Yes | Yes |
| 2 | No | NA | NO |
| 3 | Yes | NO | Yes |

Table 4 is created by one or more engines 170 based on further analytics/processing of info in Table 1, Table 2 and Table 3. In one example, Table 4 is automatically configured to have a column for screwing to motherboard. In frames 1 and 3 since hand is moving (see Table 2) and screw present (see Table 1), then screwing to motherboard (see Table 3). In frame 2, since hand is not moving (see Table 2) and screw not present (see Table 1), then no screwing to motherboard (see Table 3).

Table 4 is also automatically configured to have a column for human action safe. In frame 1 since leg not moving in frame (see Table 2) the worker is safely (see Table 3) standing at workstation while engage in activity of screwing to motherboard. In frame 3 since leg moving (see Table 2) the worker is not safely (see Table 3) standing at workstation while engage in activity of screwing to motherboard.

The one or more analytics units 525 can also be coupled to one or more front-end units 580. The one or more front-end units 575 can include a mentor portal 580, a management portal 585, and other similar portals. The mentor portal 550 can be configured for presenting feedback generated by the one or more analytics units 525 and or the one or more front-end units 575 to one or more actors. For example, the mentor portal 580 can include a touch screen display for indicating discrepancies in the processes, actions, sequences, objects and parameters at a corresponding station. The mentor portal 580 could also present training content generated by the one or more analytics units 525 and or the one or more front-end units 575 to an actor at a corresponding station. The management port 585 can be configured to enable searching of the one or more data structures storing analytics, data sets and sensor streams. The management port 585 can also be utilized to control operation of the one or more analytics units 525 for such functions as generating training content, creating work charts, performing line balancing analysis, assessing ergonomics, creating job assignments, performing causal analysis, automation analysis, presenting aggregated statistics, and the like.

The action recognition and analytics system 500 can non-intrusively digitize processes, actions, sequences, objects, parameters and the like performed by numerous entities, including both humans and machines, using machine learning. The action recognition and analytics system 500 enables human activity to be measured automatically, continuously and at scale. By digitizing the performed processes, actions, sequences, objects, parameters, and the like, the action recognition and analytics system 500 can optimize manual and/or automatic processes. In one instance, the action recognition and analytics system 500 enables the creation of a fundamentally new data set of human activity. In another instance, the action recognition and analytics system 500 enables the creation of a second fundamentally new data set of man and machine collaborating in activities. The data set from the action recognition and analytics system 500 includes quantitative data, such as which actions were performed by which person, at which station, on which specific part, at what time. The data set can also include judgements based on performance data, such as does a given person perform better or worse than average. The data set can also include inferences based on an understanding of the process, such as did a given product exit the assembly line with one or more incomplete tasks.

Figure 7:
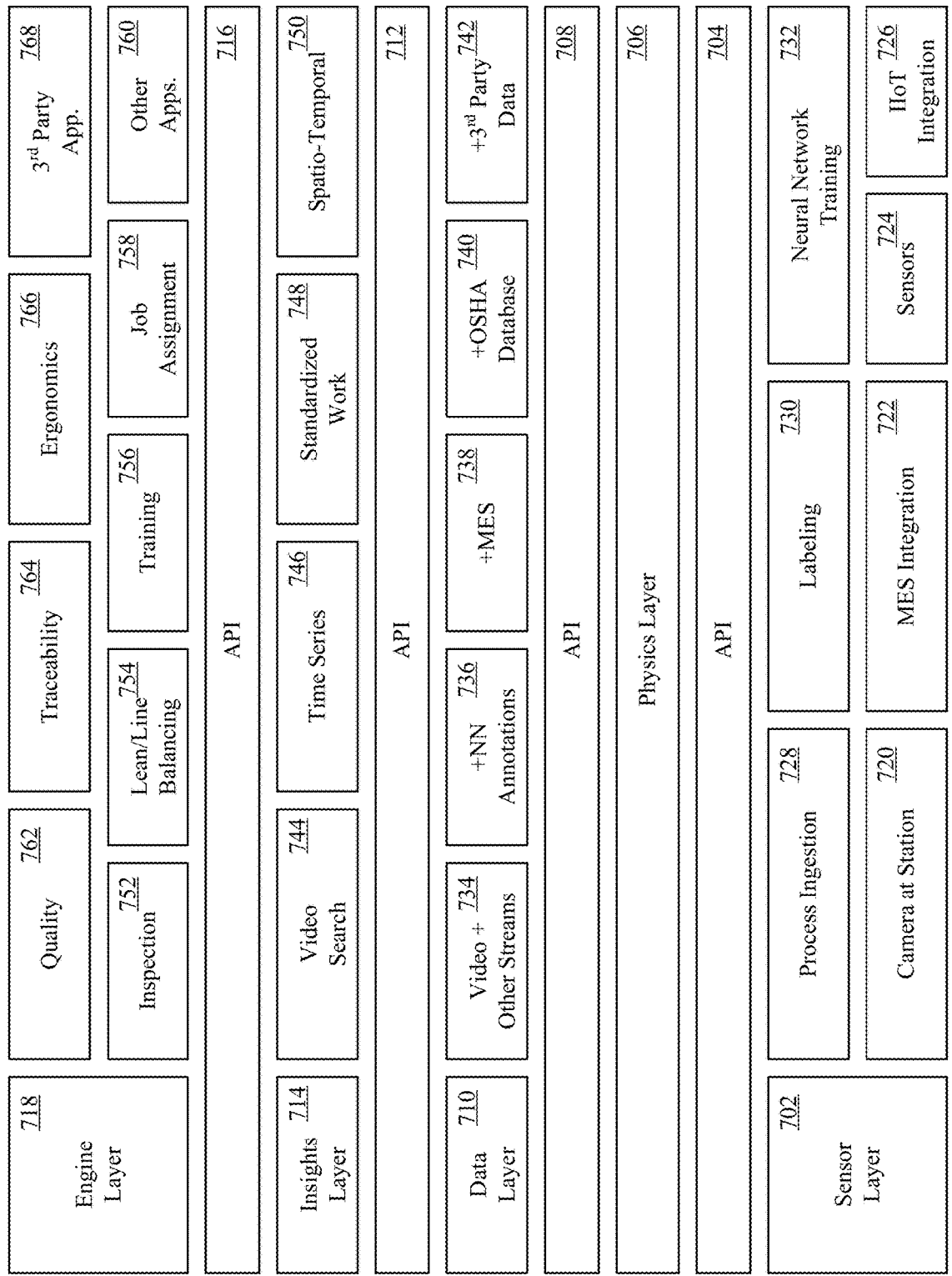
FIG. 7 shows an action recognition and analytics system, in accordance with aspects of the present technology.

Referring now to FIG. 7, an action recognition and analytics system, in accordance with aspects of the present technology, is shown. The action recognition and analytics system can include a plurality of sensor layers 702, a first Application Programming Interface (API) 704, a physics layer 706, a second API 708, a plurality of data 710, a third API 712, a plurality of insights 714, a fourth API 716 and a plurality of engine layers 718. The sensor layer 702 can include, for example, cameras at one or more stations 720, MES stations 722, sensors 724, IoT integrations 726, process ingestion 728, labeling 730, neural network training 732 and or the like. The physics layer 706 captures data from the sensor layer 702 to passes it to the data layer 710. The data layer 710, can include but not limited to, video and other streams 734, +NN annotations 736, +MES 738, +OSHA database 740, and third-party data 742. The insights layer 714 can provide for video search 744, time series data 746, standardized work 748, and spatiotemporal 842. The engine layer 718 can be utilized for inspection 752, lean/line balancing 754, training 756, job assignment 758, other applications 760, quality 763, traceability 764, ergonomics 766, and third party applications 768.

Figure 8:
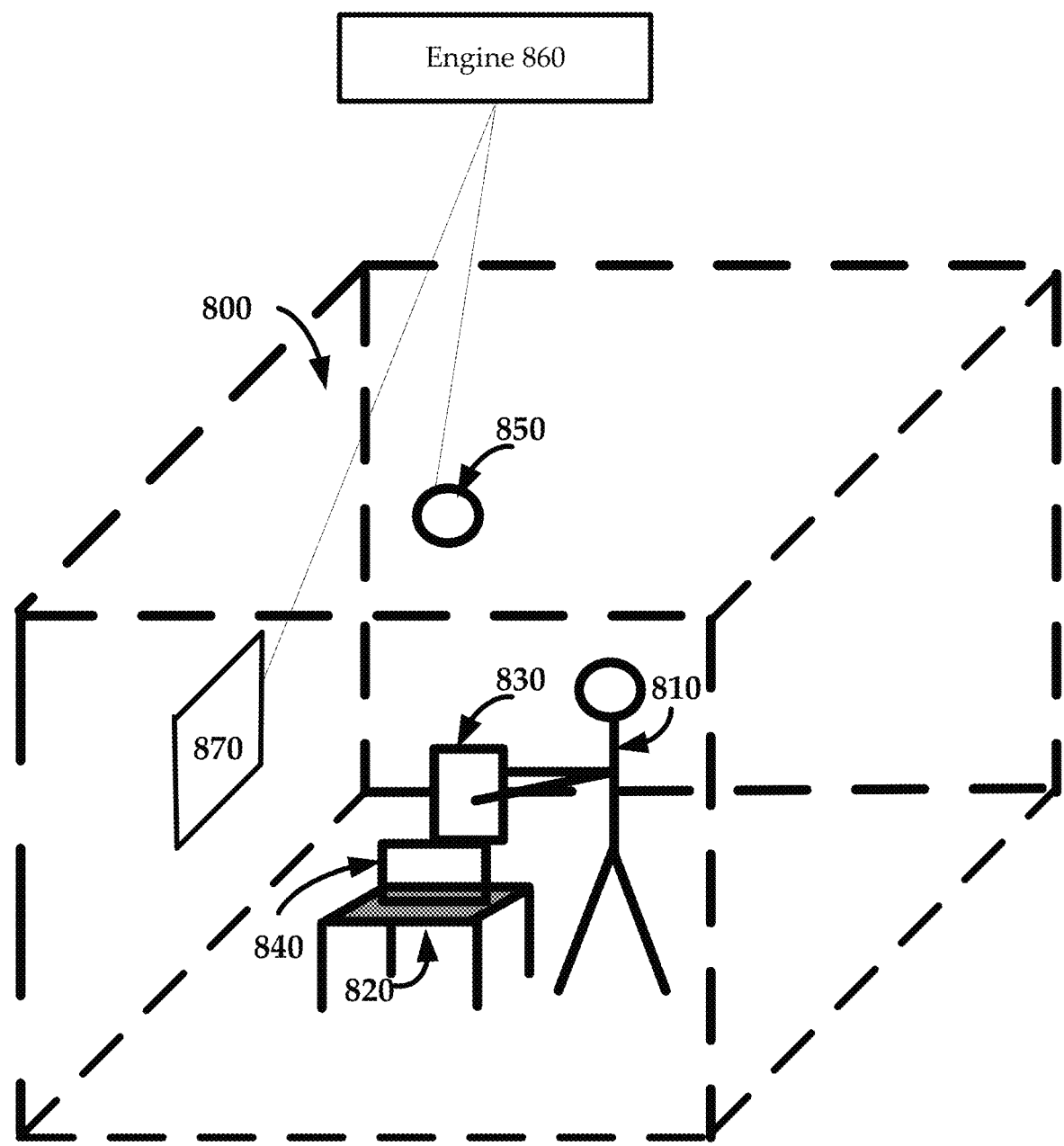
FIG. 8 shows an exemplary station, in accordance with aspects of the present technology.

Referring now to FIG. 8, an exemplary station, in accordance with aspects of the present technology, is shown. The station 800 is an area associated with one or more cycles, processes, actions, sequences, objects, parameters and or the like, herein also referred to as activity. Information regarding a station can be gathered and analyzed automatically. The information can also be gathered and analyzed in real time. In one exemplary implementation, an engine participates in the information gathering and analysis. The engine can use Artificial Intelligence to facilitate the information gathering and analysis. It is appreciated there can be many different types of stations with various associated entities and activities. Additional descriptions of stations, entities, activities, information gathering, and analytics are discussed in other sections of this detailed description.

A station or area associated with an activity can include various entities, some of which participate in the activity within the area. An entity can be considered an actor, an object, and so on. An actor can perform various actions on an object associated with an activity in the station. It is appreciated a station can be compatible with various types of actors (e.g., human, robot, machine, etc.). An object can be a target object that is the target of the action (e.g., thing being acted on, a product, a tool, etc.). It is appreciated that an object can be a target object that is the target of the action and there can be various types of target objects (e.g., component of a product or article of manufacture, an agricultural item, part of a thing or person being operated on, etc.). An object can be a supporting object that supports (e.g., assists, facilitates, aids, etc.) the activity. There can be various types of supporting objects, including load bearing components (e.g., a work bench, conveyor belt, assembly line, table top etc.), a tool (e.g., drill, screwdriver, lathe, press, etc.), a device that regulates environmental conditions (e.g., heating ventilating and air conditioning component, lighting component, fire control system, etc.), and so on. It is appreciated there can be many different types of stations with a various entities involved with a variety of activities.

Additional descriptions of the station, entities, and activities are discussed in other sections of this detailed description.

The station 800 can include a human actor 810, supporting object 820, and target objects 830 and 840. In one embodiment, the human actor 810 is assembling a product that includes target objects 830, 840 while supporting object 820 is facilitating the activity. In one embodiment, target objects 830, 840 are portions of a manufactured product (e.g., a motherboard and a housing of an electronic component, a frame and a motor of a device, a first and a second structural member of an apparatus, legs and seat portion of a chair, etc.). In one embodiment, target objects 830, 840 are items being loaded in a transportation vehicle. In one embodiment, target objects 830, 840 are products being stocked in a retail establishment. Supporting object 820 is a load bearing component (e.g., a work bench, a table, etc.) that holds target object 840 (e.g., during the activity, after the activity, etc.). Sensor 850 senses information about the station (e.g., actors, objects, activities, actions, etc.) and forwards the information to one or more engines 860. Sensor 850 can be similar to sensor 135. Engine 860 can include a machine learning back end component, analytics, and front end similar to machine learning back end unit 180, analytics unit 190, and front end 190. Engine 860 performs analytics on the information and can forward feedback to feedback component 870 (e.g., a display, speaker, etc.) that conveys the feedback to human actor 810.

Figure 9:
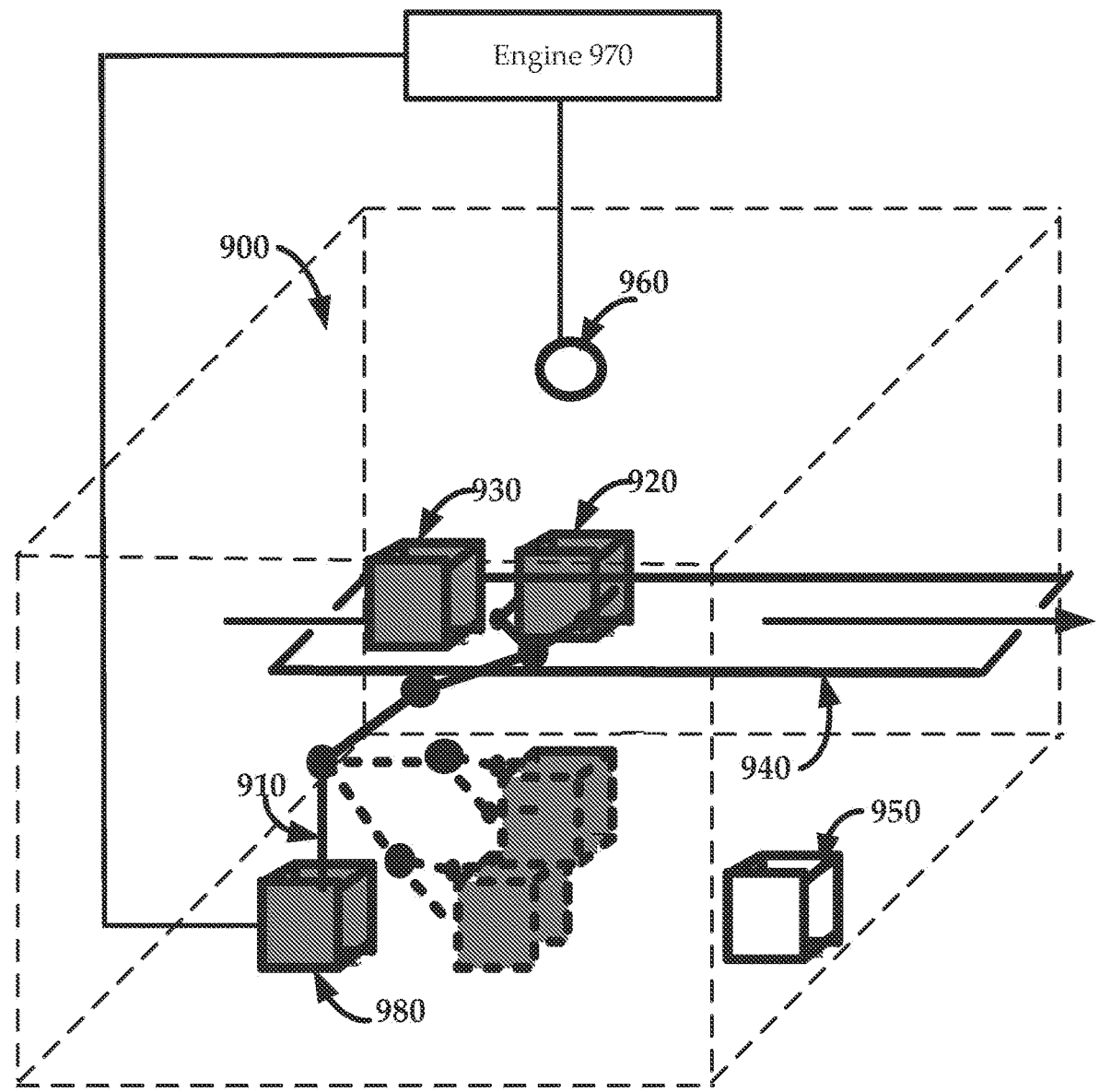
FIG. 9 shows an exemplary station, in accordance with aspects of the present technology.

Referring now to FIG. 9, an exemplary station, in accordance with aspects of the present technology, is shown. The station 900 includes a robot actor 910, target objects 920, 930, and supporting objects 940, 950. In one embodiment, the robot actor 910 is assembling target objects 920, 930 and supporting objects 940, 950 are facilitating the activity. In one embodiment, target objects 920, 930 are portions of a manufactured product. Supporting object 940 (e.g., an assembly line, a conveyor belt, etc.) holds target objects 920, 930 during the activity and moves the combined target object 920, 930 to a subsequent station (not shown) after the activity. Supporting object 940 provides area support (e.g., lighting, fan temperature control, etc.). Sensor 960 senses information about the station (e.g., actors, objects, activities, actions, etc.) and forwards the information to engine 970. Engine 970 performs analytics on the information and forwards feedback to a controller 980 that controls robot 910. Engine 970 can be similar to engine 170 and sensor 960 can be similar to sensor 135.

A station can be associated with various environments. The station can be related to an economic sector. A first economic sector can include the retrieval and production of raw materials (e.g., raw food, fuel, minerals, etc.). A second economic sector can include the transformation of raw or intermediate materials into goods (e.g., manufacturing products, manufacturing steel into cars, manufacturing textiles into clothing, etc.). A third sector can include the supply and delivery of services and products (e.g., an intangible aspect in its own right, intangible aspect as a significant element of a tangible product, etc.) to various parties (e.g., consumers, businesses, governments, etc.). In one embodiment, the third sector can include sub sectors. One sub sector can include information and knowledge-based services. Another sub sector can include hospitality and human services. A station can be associated with a segment of an economy (e.g., manufacturing, retail, warehousing, agriculture, industrial, transportation, utility, financial, energy, healthcare, technology, etc,). It is appreciated there can be many different types of stations and corresponding entities and activities. Additional descriptions of the station, entities, and activities are discussed in other sections of this detailed description.

Figure 10:
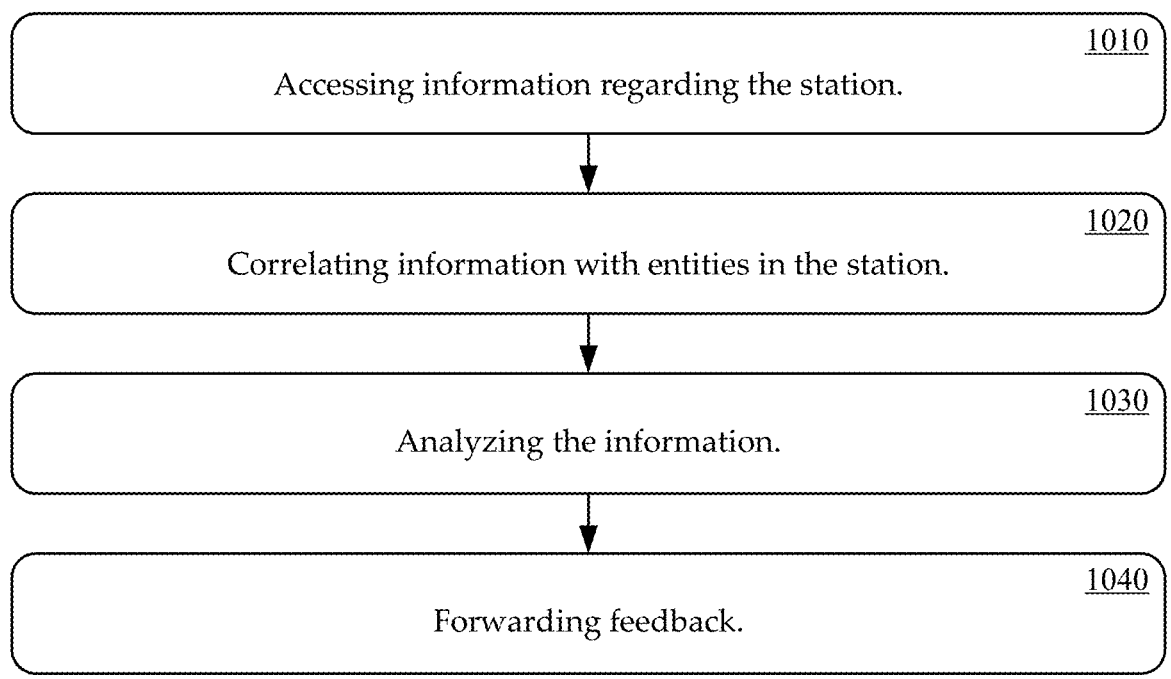
FIG. 10 shows an exemplary station activity analysis method, in accordance with one embodiment.

In one embodiment, station information is gathered and analyzed. In one exemplary implementation, an engine (e.g., an information processing engine, a system control engine, an Artificial Intelligence engine, etc.) can access information regarding the station (e.g., information on the entities, the activity, the action, etc.) and utilizes the information to perform various analytics associated with the station. In one embodiment, engine can include a machine learning back end unit, analytics unit, front end unit, and data storage unit similar to machine learning back end 180, analytics 185, front end 190 and data storage 175. In one embodiment, a station activity analysis process is performed. Referring now to FIG. 10, an exemplary station activity analysis method, in accordance with one embodiment, is shown.

At 1010, information regarding the station is accessed. In one embodiment, the information is accessed by an engine. The information can be accessed in real time. The information can be accessed from monitors/sensors associated with a station. The information can be accessed from an information storage repository. The information can include various types of information (e.g., video, thermal. optical, etc.). Additional descriptions of the accessing information are discussed in other sections of this detailed description At 1020, information is correlated with entities in the station and optionally with additional data sources. In one embodiment, the information the correlation is established at least in part by an engine. The engine can associate the accessed information with an entity in a station. An entity can include an actor, an object, and so on. Additional descriptions of the correlating information with entities are discussed in other sections of this detailed description.

At 1030, various analytics are performed utilizing the accessed information at 1010, and correlations at 1020. In one embodiment, an engine utilizes the information to perform various analytics associated with station. The analytics can be directed at various aspects of an activity (e.g., validation of actions, abnormality detection, training, assignment of actor to an action, tracking activity on an object, determining replacement actor, examining actions of actors with respect to an integrated activity, automatic creation of work charts, creating ergonomic data, identify product knitting components, etc.) Additional descriptions of the analytics are discussed in other sections of this detailed description.

At 1040, optionally, results of the analysis can be forwarded as feedback. The feedback can include directions to entities in the station. In one embodiment, the information accessing, analysis, and feedback are performed in real time. Additional descriptions of the station, engine, entities, activities, analytics and feedback are discussed in other sections of this detailed description, It is also appreciated that accessed information can include general information regarding the station (e.g., environmental information, generic identification of the station, activities expected in station, a golden rule for the station, etc.). Environmental information can include ambient aspects and characteristics of the station (e.g., temperature, lighting conditions, visibility, moisture, humidity, ambient aroma, wind, etc.).

It also appreciated that some of types of characteristics or features can apply to a particular portion of a station and also the general environment of a station. In one exemplary implementation, a portion of a station (e.g., work bench, floor area, etc.) can have a first particular visibility level and the ambient environment of the station can have a second particular visibility level. It is appreciated that some of types of characteristics or features can apply to a particular entity in a station and also the station environment. In one embodiment, an entity (e.g., a human, robot, target object, etc.) can have a first particular temperature range and the station environment can have a second particular temperature range.

The action recognition and analytics system 100, 500 can be utilized for process validation, anomaly detection and/or process quality assurance in real time. The action recognition and analytics system 100, 500 can also be utilized for real time contextual training. The action recognition and analytics system 100, 500 can be configured for assembling training libraries from video clips of processes to speed new product introductions or onboard new employees. The action recognition and analytics system 100, 500 can also be utilized for line balancing by identifying processes, sequences and/or actions to move among stations and implementing lean processes automatically. The action recognition and analytics system 100, 500 can also automatically create standardized work charts by statistical analysis of processes, sequences and actions. The action recognition and analytics system 100, 500 can also automatically create birth certificate videos for a specific unit. The action recognition and analytics system 100, 500 can also be utilized for automatically creating statistically accurate ergonomics data. The action recognition and analytics system 100, 500 can also be utilized to create programmatic job assignments based on skills, tasks, ergonomics and time. The action recognition and analytics system 100, 500 can also be utilized for automatically establishing traceability including for causal analysis. The action recognition and analytics system 100, 500 can also be utilized for kitting products, including real time verification of packing or unpacking by action and image recognition. The action recognition and analytics system 100, 500 can also be utilized to determine the best robot to replace a worker when ergonomic problems are identified. The action recognition and analytics system 100, 500 can also be utilized to design an integrated line of humans and robot and/or robots. The action recognition and analytics system 100, 500 can also be utilized for automatically programming robots based on observing non-modeled objects in the work space.

In various embodiments, one or more engines (e.g., described herein) can also be utilized for line balancing by identifying processes, sequences and/or actions to move among stations and implementing a lean process automatically.

A line balancing system in accordance with various embodiments of the present disclosure is able to continuously gather data (e.g., one or more streams of data) at all times that the line is running, including sampling one or more video streams at tens of frames per second, but is not limited to such. Further, a line balancing system in accordance with various embodiments is able to automatically break this data down into the underlying tasks. Therefore, a line balancing system in accordance with various embodiments is able to deliver time and motion data at a level of granularity never before possible. It is noted that a line balancing system in accordance with various embodiments can be implemented with one or more engines as described herein, but is not limited to such. Further, in various embodiments, the rebalancing can be done dynamically or over longer periods of time.

A line balancing system in accordance with various embodiments of the present disclosure directly benefits from one or more engines (e.g., described herein), which extracts action information and one or more finite state machine systems. The action information, depending on the sampling rate of the vision system (or one or more sensor systems), is accurate to sub-second. For example, accurate and detailed data points for thousands of repetitions of each action (or operation of a production process) are now available. The line balancing system can create statistical measures, from this large data set, for each action in the process.

Simultaneously (or at substantially the same time) in various embodiments, the finite state machine knows of process dependencies (e.g., within the production line). For example, consider the installation of a hard drive in a server. The mounts need to be in place and attached to the chassis before a hard drive can be fastened to the mounts (and, therefore, the chassis) using four screws. In this case, there are five actions: secure the mounts to the chassis; pick up the four screws; pick up the hard drive; pick up the electric screwdriver; and, using the screwdriver, secure the hard drive using the four screws. The process is dependent on the mount being in place and is agnostic to the order in which the hard drive, screws, and screwdriver are picked up.

With the time and motion metrics and a knowledge of the process dependencies in hand, the line balancing system in accordance with various embodiments is able to propose one or more optimal reallocation of actions (or tasks or steps or operations) so the cycle time at every station is probabilistically (e.g., to some pre-determined confidence level) at or below the takt time for each action or task. It is noted that the line balancing system in accordance with various embodiments can optimize across all the stations on a line, globally or locally, sequentially or non-sequentially, off-line or in real-time, moving one or more actions (or tasks) to a different station of a production line than initially assigned, but is not limited to such. And, when done, each station is balanced and there is the distinct possibility, depending on how much waste there was in the original production line, of eliminating one or more stations of the production line.

Simultaneously (or at substantially the same time) in various embodiments, the one or more finite state machines of the line balancing system knows of process dependencies (e.g., within the production line). With the time and motion metrics and a knowledge of the process dependencies in hand, the line balancing system in accordance with various embodiments is able to propose one or more optimal designs for a new product introduction on an existing line. Additionally, the line balancing system can propose optimal designs for new lines which involve substantially the same sets of actions for which the line balancing system has collected data in the past. In these embodiments, the line balancing system can substantially improve upon the efficiency of the traditional iterative process of assembly line design.

In addition, in various embodiments, the line balancing system incorporates various constraints inherent to any sequential process or assembly line—certain tasks can only be performed in a certain order (for example hard drive mounts must be secured into the chassis before a hard drive can be affixed to them with screws), certain tasks can only be performed at certain stations because the equipment required for said tasks is fixed to certain stations, cost constraints having to do with labor, machine operation or materials costs as well as time and space constraints having to do with materials storage and delivery. In various embodiments, the line balancing system can incorporate some or all of these constraints into the solution process. In addition, in various embodiments, the optimization algorithm used by the line balancing system can rebalance the line at different time frames. It is often possible, but not necessary, that re-balancing time constraints can lead to tradeoffs in the quality of the solution being generated. Therefore, rapid, real time optimization can be done to tide through the current needs while a more accurate process can be run and deployed at a later time (e.g., in time for the next shift). More generally, different constraints can be incorporated into the optimization performed by the line balancing system depending upon the timescale being considered.

In addition, in various embodiments, a constrained optimization tool (e.g., linear programming, genetic algorithms, dynamic programming, branch and bound methods, etc.), heuristic approaches or simulation based approaches (e.g., Monte Carlo methods) can be used by a line balancing system to mathematically or programmatically determine a more optimal re-allocation of actions (or operations or tasks) to stations on the production line. Given that the data that the line balancing system is gathering reflects the variability in the process, the line balancing algorithm incorporates information about the statistical nature of the data in the solution process.

In various embodiments, the statistical characteristics of the task data, especially the nature of the variability of the task performance times can involve a novel constrained optimization algorithm which utilizes a new framework to reflect these statistical characteristics. New mathematical techniques are combined with certain existing techniques listed above (in current or modified forms) to implement this framework to solve the line balancing problem. In various embodiments, a line balancing system can implement the following: Given a directed acyclic graph G=(A,P) where the nodes $A_i$ represent the actions, and the arrows P represent the precedence relations between the actions, the line balancing system tries to divide the tasks $A_i$ into K groups (stations) such that the precedence relations $P_j$ are respected. Given statistical distributions of task times $d_i(t)$ with means $t_i$ corresponding to the actions $A_i$, the time to perform all the tasks to be performed at station j is $$S_j = \sum_{i=1}^{N_j} t_i \text{ where } A_i \in \text{Station } j$$

Figure 11:
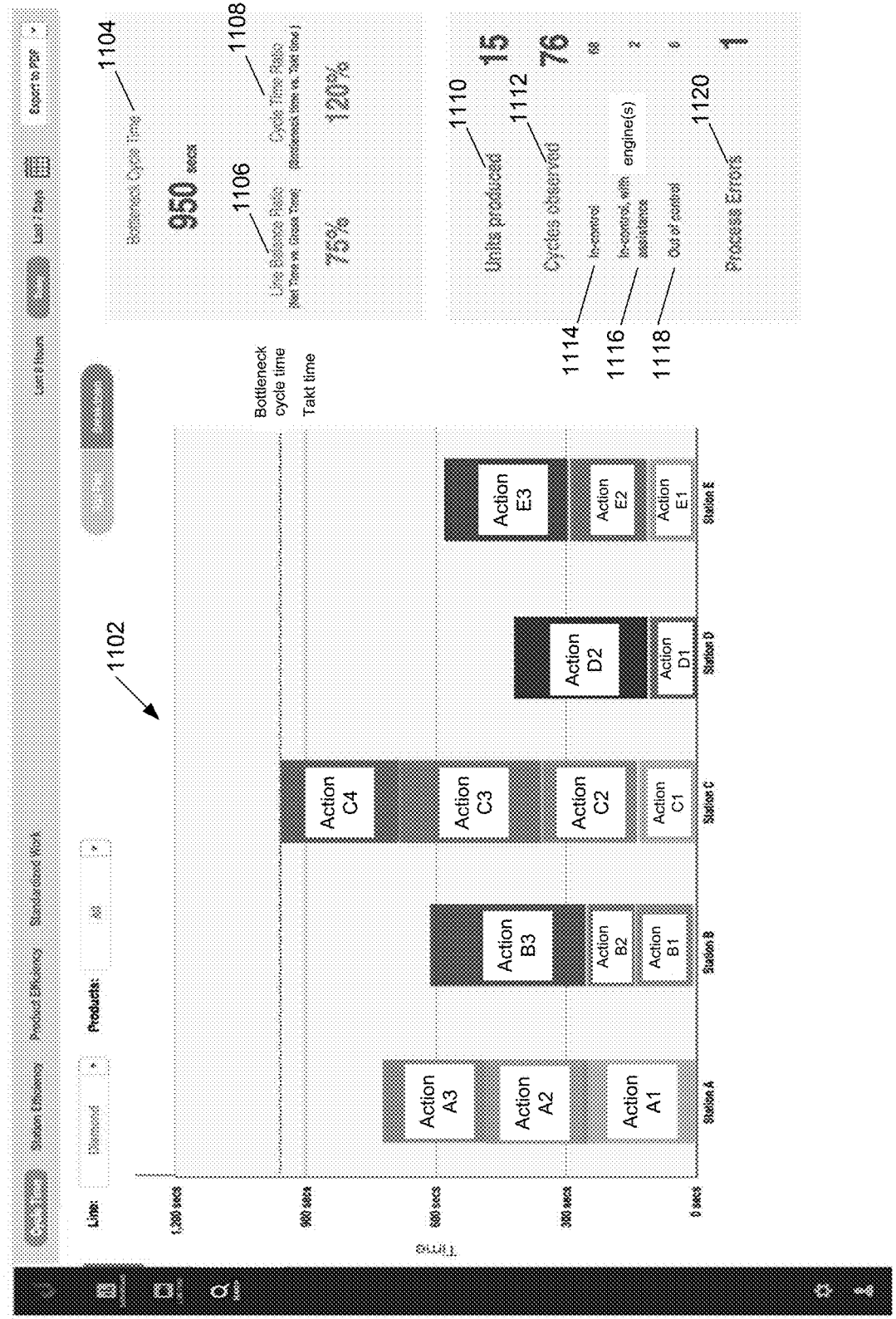
FIG. 11 illustrates a dashboard interface in accordance with various embodiments of the present disclosure.

The cycle time C is the amount of time available to complete the task at each station. In one embodiment, the optimization problem can be defined as the task of minimizing the idle time $(C-S_j)$ for each station subject to the precedence relations P. In other embodiments, a line balancing system may choose to minimize either the idle time or other similar expressions to a given confidence level determined by the distributions $d_i(t)$ and adding additional heuristics about line functionality FIG. 11 illustrates a dashboard interface 1100 in accordance with various embodiments of the present disclosure that shows time taken for each action (or task) at each station of a production line, manufacturing, health care, warehousing, shipping, retail, or similar context. In various embodiments, the dashboard interface 1100 can be implemented as a Graphical User Interface (GUI) that is produced by one or more computing devices (e.g., one or more engines). Specifically, the dashboard interface 1100 can include a graph 1102 wherein the Y-axis represents time in seconds (sec) while the X-axis identifies each station of a production line, manufacturing, health care, warehousing, shipping, retail, or similar context, but is not limited to such. In addition, it is noted that each action (or task) block of the graph 1102 represents an action (or task) performed at each station. Furthermore, the height of each action block represents the time taken to complete that corresponding action of the production line, manufacturing, health care, warehousing, shipping, retail, or similar context. In various embodiments, each station of the plurality of stations of dashboard interface 1100 can be understood as a specific location where one or more actions occur.

Within the graph 1102 of the dashboard interface 1100, it appears the cycle time taken to complete Actions A1, A2, and A3 at Station A is approximately 690 seconds while the cycle time taken to complete Actions B1, B2, and B3 at Station B is approximately 600 seconds. In addition, it appears the cycle time taken to complete Actions C1, C2, C3, and C4 at Station C is 950 seconds while the cycle time taken to complete Actions D1 and D2 at Station D is approximately 425 seconds. Furthermore, it appears the cycle time taken to complete Actions E1, E2, and E3 at Station E is less than 600 seconds. In various embodiments, the dashboard 1100 can include a "Bottleneck Cycle Time" 1104 of the production line, manufacturing, health care, warehousing, shipping, retail, or similar context, which is currently equal to 950 second and corresponds to the cycle time of completing Actions C1, C2, C3, and C4 at Station C. Additionally, note that it is undesirable that the Bottleneck Cycle Time 1104 is equal to 950 seconds since it is greater than a predetermined takt time of 900 seconds.

With reference to FIG. 11, within various embodiments, the dashboard interface 1100 can also include additional information such as, but not limited to, "Line Balance Ratio" 1106, "Cycle Time Ratio" 1108, "Units produced" 1110, "Cycles observed" 1112, "Process Errors" 1120. Furthermore, the dashboard interface 1100 can also include sub-category information for the "Cycles observed" 1112 such as, but not limited to, "In-control" 1114, "In-control, with system assistance" 1116, and "Out of control" 1118.

Within the present embodiment of the dashboard interface 1100, the Line Balance Ratio 1106 is currently equal to 75% and can be defined as a net time of a production line versus a gross time of the production line, but is not limited to such. Additionally, the Cycle Time Ratio 1108 is currently equal to 120% and can be defined as a bottleneck time of the production line versus a takt time of the production line, but is not limited to such.

It is noted that the description of the dashboard interface 1100 herein includes some references to a production line. However, the dashboard interface 1100 is not in any way limited to implementation with a production line. As mentioned herein, in various embodiments the dashboard interface 1100 can also be implemented for manufacturing, health care, warehousing, shipping, retail, or similar context.

Figure 12:
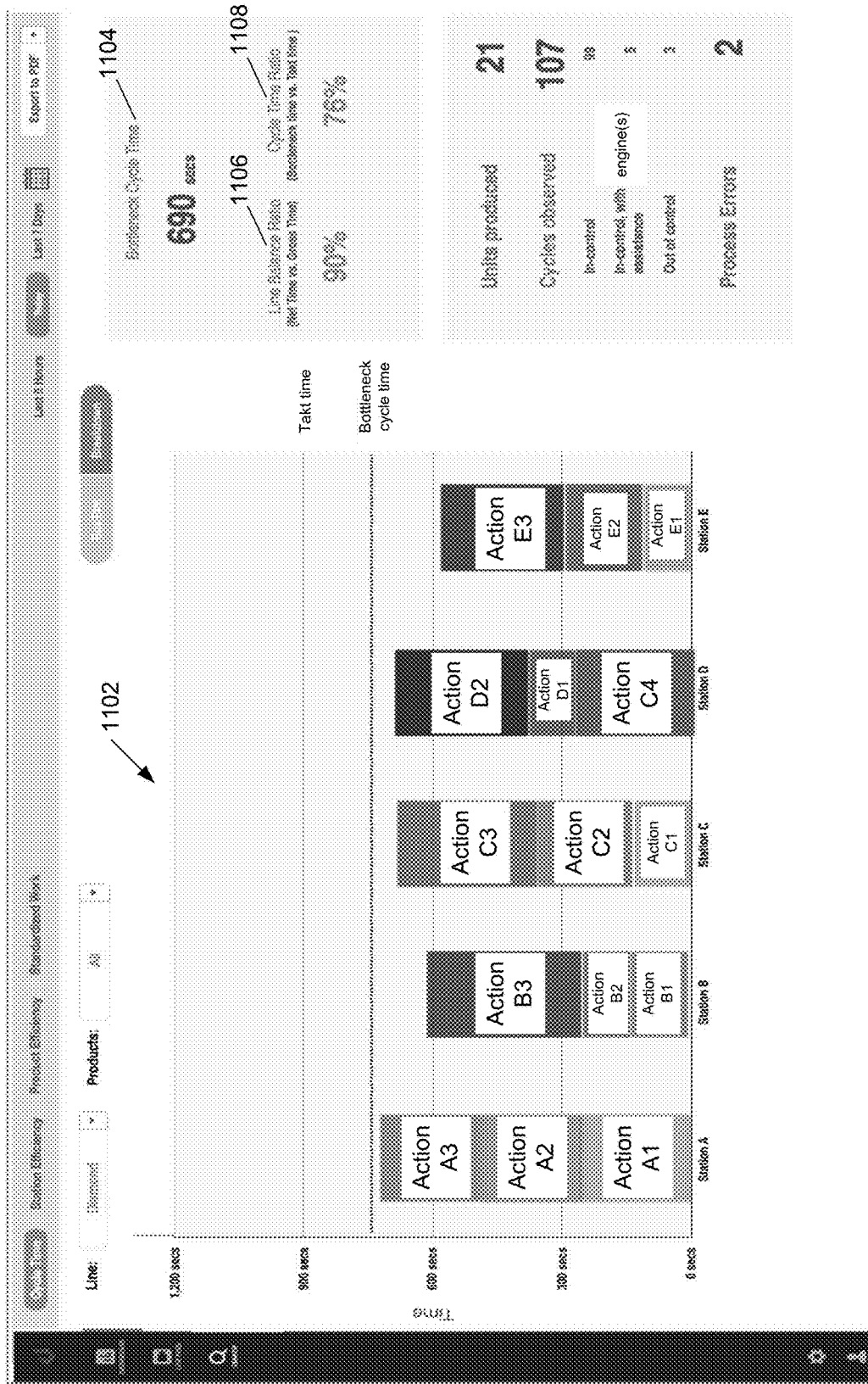
FIG. 12 illustrates the dashboard interface in accordance with various embodiments of the present disclosure.

FIG. 12 illustrates the dashboard interface 1100 in accordance with various embodiments of the present disclosure can recommend moving one or more actions (or operations or tasks) of the production line to optimally reduce cycle time for the given line configuration. Note that the dashboard interface 1100 is a part of a line balancing system in accordance with various embodiments of the present disclosure. As described herein, with the time and motion metrics and a knowledge of the process dependencies of the production line, the line balancing system in various embodiments can propose a more optimal reallocation of actions within the graph 1102 so the cycle time at every station is probabilistically (e.g., to some pre-determined confidence level) at or below the takt time for each action or task. In various embodiments, the proposal of a more optimal real-location of actions can take the form of a recommendation by the dashboard interface 1100 with the graph 1102. Moreover, the line balancing system in various embodiments can move from optimizing the first station to the last station, moving one or more actions (or tasks or operations) to a different station of a production line than initially assigned, but is not limited to such. And, when done, each station is balanced.

For example, note that the dashboard interface 1100 of FIG. 12 has produced (or proposed) a visual recommendation via the graph 1102 to more optimally re-allocate the Action C4 that was performed at Station C to be performed at Station D. Specifically, the dashboard interface 1100 of FIG. 12 via the graph 1102 recommends moving the Action D4 to be performed at Station D before Action D1 and Action D2. Therefore, as shown in FIG. 12, it appears the cycle time taken to complete Actions C4, D1, and D2 at Station D is less than 690 seconds, which is advantageously less than the predetermined takt time of 900 seconds. Note that in various embodiments, the dashboard interface 1100 (e.g., under the direction of one or more engines described herein) can recommend moving one or more actions from a station to any other stations (e.g., upstream stations, downstream stations, or any combination thereof).

Within FIG. 12, it is noted that the dashboard interface 1100 indicates as part of the recommendation that the Bottleneck Cycle Time 1104 of the production line would currently be equal to 690 seconds. In addition, the dashboard interface 1100 also indicates as part of the recommendation that the Line Balance Ratio 1106 would currently be equal to 90% and the Cycle Time Ratio 1108 would currently be equal to 76%.

Figure 13:
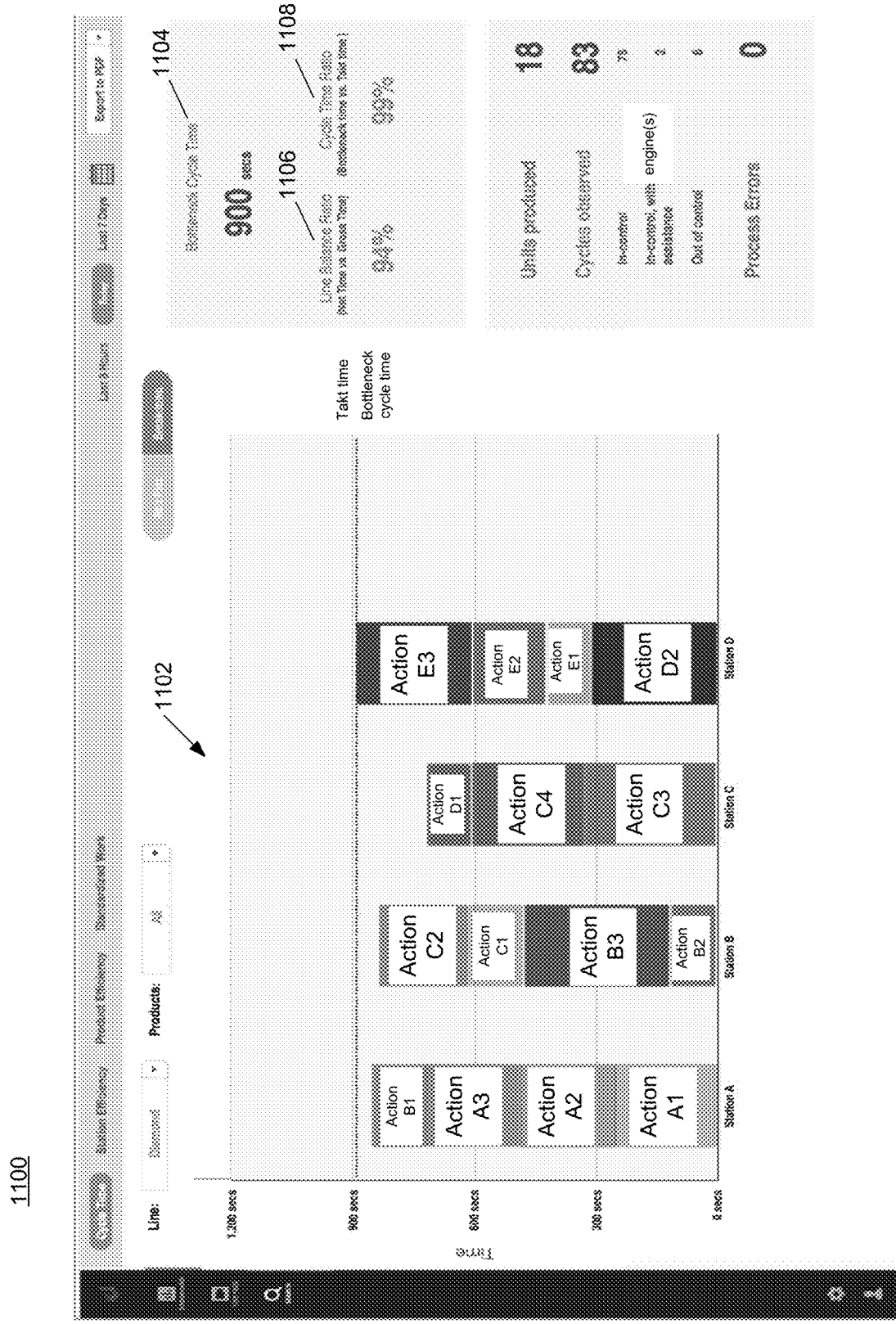
FIG. 13 illustrates the dashboard interface in accordance with various embodiments of the present disclosure.

FIG. 13 illustrates the dashboard interface 1100 in accordance with various embodiments of the present disclosure can also recommend moving one or more actions (or operations or tasks) from one or more stations to one or more stations to eliminate one or more stations (e.g., the stations at the end of the line). It is noted that the dashboard interface 1100 is a part of the line balancing system in accordance with various embodiments of the present disclosure.

For example, the dashboard interface 1100 of FIG. 13 via graph 1102 can recommend (or propose) moving Action B1 from Station B to instead be performed at Station A. Specifically, at Station A, Action B1 would be performed after Actions A1, A2, and A3 are performed at Station A. Furthermore, the dashboard interface 1100 of FIG. 13 via graph 1102 can recommend (or propose) moving Actions C1 and C2 from Station C to instead be performed at Station B. Specifically, at Station B, Actions C1 and C2 would be performed after Actions B2, and B3 are performed at Station B. Moreover, the dashboard interface 1100 of FIG. 13 via graph 1102 can recommend (or propose) moving Action D1 from Station D to instead be performed at Station C. Specifically, at Station C. Actions D1 would be performed after Actions C3 and C4 are performed at Station C. In addition, the dashboard interface 1100 of FIG. 13 via graph 1102 can recommend (or propose) moving Actions E1, E2, and E3 from Station E to instead be performed at Station D. Specifically, at Station D. Actions E1, E2, and E3 would be performed after Action D2 is performed at Station D. Based on these recommendations of the dashboard interface 1100 of FIG. 13 via graph 1102, note that Station E has advantageously been eliminated from the production line. However, it is noted that the dashboard interface 1100 via graph 1102 can recommend moving one or more actions among stations resulting in the elimination of any one or more stations of a production line, manufacturing, health care, warehousing, shipping, retail, or similar context.

Within FIG. 13, it is noted that the dashboard interface 1100 also indicates as part of the recommendation that the Bottleneck Cycle Time 1104 of the production line would currently be equal to 900 seconds, which is advantageously equal to the predetermined takt time of 900 seconds. Moreover, the dashboard interface 1100 also advantageously indicates as part of the recommendations that the Line Balance Ratio 1106 would currently be equal to 94% and the Cycle Time Ratio 1108 would currently be equal to 99%.

It is noted that the dashboard interface 1100 may not include all of the elements illustrated by FIGS. 11, 12, and 13. In addition, the dashboard interface 1100 can be implemented to include one or more elements not illustrated by FIGS. 11, 12, and 13. It is pointed out that the dashboard interface 1100 can be utilized or implemented in any manner similar to that described and/or shown by the present disclosure, but is not limited to such.

FIG. 14 is a flow diagram of a method 1400 for line balancing by identifying processes, sequences and/or actions to move among stations and implementing a lean process automatically in accordance with various embodiments of the present disclosure. Although specific operations are disclosed in FIG. 14, such operations are examples. The method 1400 may not include all of the operations illustrated by FIG. 14. Also, method 1400 may include various other operations and/or variations of the operations shown. Likewise, the sequence of the operations of flow diagram 1400 can be modified. It is appreciated that not all of the operations in flow diagram 1400 may be performed. In various embodiments, one or more of the operations of method 1400 can be controlled or managed by one or more engines (as described herein), by software, by firmware, by hardware or by any combination thereof, but is not limited to such. Method 1400 can include processes of various embodiments of the present disclosure which can be controlled or managed by a processor(s) and electrical components under the control of computer or computing device readable and executable instructions or code. The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory.

At operation 1402, one or more sensor streams can be received by one or more engines as described herein. Note that operation 1402 can be implemented in a wide variety of ways. For example, the one or more sensor streams at operation 1402 can include one or more of: video frames, thermal sensor data, force sensor data, audio sensor data, haptic data, and light sensor data, but is not limited to such. Furthermore, the one or more sensor streams at operation 1402 can be associated with a plurality of stations where one or more actions occur at each station, but are not limited to such. It is noted that operation 1402 can be implemented in any manner similar to that described and/or shown by the present disclosure, but is not limited to such.

At operation 1404 of FIG. 14, the one or more engines are utilized to identify one or more actions that are performed at a first station of a plurality of stations within the one or more sensor streams. It is noted that operation 1404 can be implemented in a wide variety of ways. For example, in various embodiments, the plurality of stations of method 1400 can be implemented as part of a production line, manufacturing, health care, warehousing, shipping, retail, or similar context, but is not limited to such. In addition, in various embodiments, each station of the plurality of stations of method 1400 can be understood as a location where one or more actions (e.g., sequential and/or non-sequential) occur. Moreover, in various embodiments, the plurality of stations of method 1400 can include two or more stations. Note that operation 1404 can be implemented in any manner similar to that described and/or shown by the present disclosure, but is not limited to such.

At operation 1406, the one or more engines are utilized to identify one or more actions that are performed at a second station of the plurality of stations within the one or more sensor streams. Note that operation 1406 can be implemented in a wide variety of ways. For example, in various embodiments, the second station of operation 1406 can be sequentially after or before the first station of the plurality of stations. Moreover, in various embodiments, the plurality of stations of method 1400 can include just the first and second stations. Furthermore, in various embodiments, the plurality of stations of method 1400 can include the first and second stations along with one or more additional stations. In addition, in various embodiments of method 1400, the first station can be sequentially after or before the second station of the plurality of stations. Furthermore, in various embodiments of method 1400, the first station and the second station of the plurality of stations are not sequential. Note that operation 1406 can be implemented in any manner similar to that described and/or shown by the present disclosure, but is not limited to such.

At operation 1408 of FIG. 14, the received one or more sensor streams, the identified one or more actions performed at the first station, and the identified one or more actions performed at the second station are stored in one or more data structures by the one or more engines. In addition, at operation 1408, it is noted that the identified one or more actions performed at each of the first and second stations are mapped or indexed to the one or more sensor streams by the one or more engines. Note that operation 1408 can be implemented in a wide variety of ways. For example, operation 1408 can be implemented in any manner similar to that described and/or shown by the present disclosure, but is not limited to such.

At operation 1410, the one or more engines are utilized to characterize each of the identified one or more actions performed at each of the first and second stations to produce determined characterizations thereof. Note that operation 1410 can be implemented in a wide variety of ways. For example, the determined characterizations at operation 1410 can include time taken to perform each of the identified one or more actions performed at each of the first and second stations. Additionally, in various embodiments, the determined characterizations at operation 1410 can include at least one action of the identified one or more actions performed at the first station or second station cannot be moved because of one or more station capability constraints (e.g., equipment and/or physical limitations associated with one or more stations). Furthermore, in various embodiments, the determined characterizations at operation 1410 can include at least one action of the identified one or more actions performed at the first station or second station cannot be moved because of one or more sequence constraints associated with one or more stations. Note that operation 1410 can be implemented in any manner similar to that described and/or shown by the present disclosure, but is not limited to such.

At operation 1412 of FIG. 14, based on one or more of the determined characterizations, a recommendation is produced automatically by the one or more engines to move at least one of the identified one or more actions performed at one of the stations to another station to reduce cycle time. It is noted that operation 1412 can be implemented in a wide variety of ways. For example, in various embodiments at operation 1412, based on one or more of the determined characterizations, a recommendation is produced automatically by the one or more engines to move at least one of the identified one or more actions performed at the first station to the second station to reduce cycle time. Furthermore, in various embodiments at operation 1412, based on one or more of the determined characterizations, a recommendation is produced automatically by the one or more engines to move at least one of the identified one or more actions performed at the second station to the first station to reduce cycle time. In various embodiments, the recommendation at operation 1412 can be produced in real-time while a line is running or offline (or post-facto or on-demand) for later implementation. In various embodiments, the recommendation at operation 1412 can be produced either dynamically or post-facto, but is not limited to such. In various embodiments, the recommendation automatically produced at operation 1412 by the one or more engines can be implemented as a visual recommendation (e.g., via one or more displays, via the dashboard interface 1100 being displayed, and the like), as an audible recommendation (e.g., via one or more speakers), as a tactile recommendation, and the like, or any combination thereof, but is not limited to such. Furthermore, the one or more of the determined characterizations at operation 1412 can include the one or more of the determined characterizations described above with reference to operation 1410, but is not limited to such. Note that the operation 1412 can be implemented in any manner similar to that described and/or shown by the present disclosure, but is not limited to such.

Figure 15:
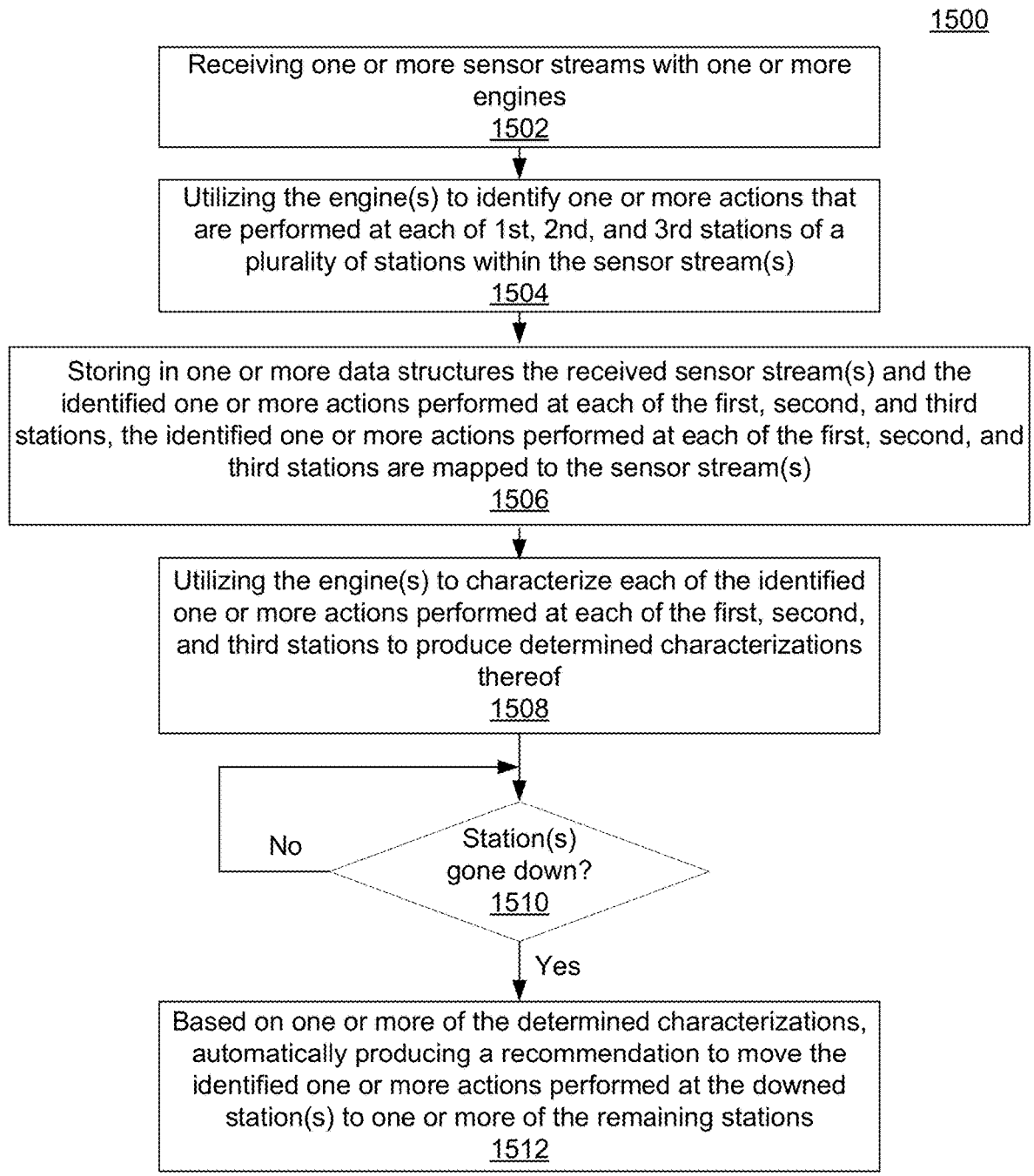
FIG. 15 is a flow chart of an exemplary method in accordance with various embodiments of the present disclosure.

FIG. 15 is a flow diagram of a method 1500 for dynamically rebalancing a line when one or more stations go down in accordance with various embodiments of the present disclosure. Although specific operations are disclosed in FIG. 15, such operations are examples. The method 1500 may not include all of the operations illustrated by FIG. 15. Also, method 1500 may include various other operations and/or variations of the operations shown. Likewise, the sequence of the operations of flow diagram 1500 can be modified. It is appreciated that not all of the operations in flow diagram 1500 may be performed. In various embodiments, one or more of the operations of method 1500 can be controlled or managed by one or more engines (as described herein), by software, by firmware, by hardware or by any combination thereof, but is not limited to such. Method 1500 can include processes of various embodiments of the present disclosure which can be controlled or managed by a processor(s) and electrical components under the control of computer or computing device readable and executable instructions or code. The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory.

At operation 1502, one or more sensor streams can be received by one or more engines as described herein. Note that operation 1502 can be implemented in a wide variety of ways. For example, the one or more sensor streams at operation 1502 can include one or more of: video frames, thermal sensor data, force sensor data, audio sensor data, haptic data, and light sensor data, but is not limited to such. In addition, the one or more sensor streams at operation 1502 can be associated with a plurality of stations where one or more actions occur at each station, but are not limited to such. It is noted that operation 1502 can be implemented in any manner similar to that described and/or shown by the present disclosure, but is not limited to such.

At operation 1504 of FIG. 15, the one or more engines are utilized to identify one or more actions that are performed at each of first, second, and third stations of a plurality of stations within the one or more sensor streams. It is noted that operation 1504 can be implemented in a wide variety of ways. For example, in various embodiments, the plurality of stations of method 1500 can be implemented as part of a production line, manufacturing, health care, warehousing, shipping, retail, or similar context, but is not limited to such. In various embodiments, the first, second, and third stations of method 1500 can be arranged in any order (e.g., the first station may be sequentially after the second and third stations, the second station may be sequentially after the first and third stations, the third station may be sequentially before the first and second stations, or the like). In addition, in various embodiments of method 1500, the first, second, and third stations of the plurality of stations are not sequential. Furthermore, in various embodiments, each station of the plurality of stations of method 1500 can be understood as a location where one or more actions (e.g., sequential and/or non-sequential) occur. Additionally, in various embodiments, the plurality of stations of method 1500 can include three or more stations. Note that operation 1504 can be implemented in any manner similar to that described and/or shown by the present disclosure, but is not limited to such.

At operation 1506, the received one or more sensor streams and the identified one or more actions performed at each of the first, second, and third stations are stored in one or more data structures by the one or more engines. Furthermore, at operation 1506, it is noted that the identified one or more actions performed at each of the first, second, and third stations are mapped or indexed to the one or more sensor streams by the one or more engines. Note that operation 1506 can be implemented in a wide variety of ways. For example, operation 1506 can be implemented in any manner similar to that described and/or shown by the present disclosure, but is not limited to such.

At operation 1508 of FIG. 15, the one or more engines are utilized to characterize each of the identified one or more actions performed at each of the first, second, and third stations to produce determined characterizations thereof. Note that operation 1508 can be implemented in a wide variety of ways. For example, the determined characterizations at operation 1508 can include time taken to perform each of the identified one or more actions performed at each of the first, second, and third stations. Additionally, in various embodiments, the determined characterizations at operation 1508 can include at least one action of the identified one or more actions performed at the first station, second station, or third station cannot be moved because of one or more station capability constraints (e.g., equipment and/or physical limitations associated with one or more stations). Furthermore, in various embodiments, the determined characterizations at operation 1508 can include at least one action of the identified one or more actions performed at the first station, second station, or third station cannot be moved because of one or more sequence constraints associated with one or more stations. Note that operation 1508 can be implemented in any manner similar to that described and/or shown by the present disclosure, but is not limited to such.

At operation 1510, a determination is made as to whether one or more stations of the first, second, and third stations has gone down or become inoperable or unusable or inactive. If not, the method 1500 proceeds to the beginning of operation 1510 to repeat it. However, if it is determined at operation 1510 that one or more stations of the first, second, and third stations have gone down or become inoperable or unusable or inactive, the method 1500 proceeds to operation 1512. Note that operation 1510 can be implemented in a wide variety of ways. For example, the determination at operation 1510 can be performed by one or more engines, but is not limited to such. Note that the operation 1510 can be implemented in any manner similar to that described and/or shown by the present disclosure, but is not limited to such.

At operation 1512 of FIG. 15, based on one or more of the determined characterizations, a recommendation is produced automatically by the one or more engines to move the identified one or more actions performed at the one or more downed stations to one or more of the remaining stations. It is noted that operation 1512 can be implemented in a wide variety of ways. For example, in various embodiments at operation 1512, based on one or more of the determined characterizations, a recommendation is produced automatically by the one or more engines to move the identified one or more actions performed at the one or more downed stations (e.g., the third station) to the one or more remaining stations (e.g., the first station and/or the second station). In various embodiments, the recommendation at operation 1512 can be produced in real-time while a line is running or offline (or post-facto or on-demand) for later implementation. In various embodiments, the recommendation at operation 1512 can be produced either dynamically or post-facto, but is not limited to such. In various embodiments, the recommendation automatically produced at operation 1512 by the one or more engines can be implemented as a visual recommendation (e.g., via one or more displays, via the dashboard interface 1100 being displayed, and the like), as an audible recommendation (e.g., via one or more speakers), as a tactile recommendation, and the like, or any combination thereof, but is not limited to such. Furthermore, the one or more of the determined characterizations at operation 1512 can include the one or more of the determined characterizations described above with reference to operation 1510, but is not limited to such. Note that the operation 1512 can be implemented in any manner similar to that described and/or shown by the present disclosure, but is not limited to such.

Figure 16:
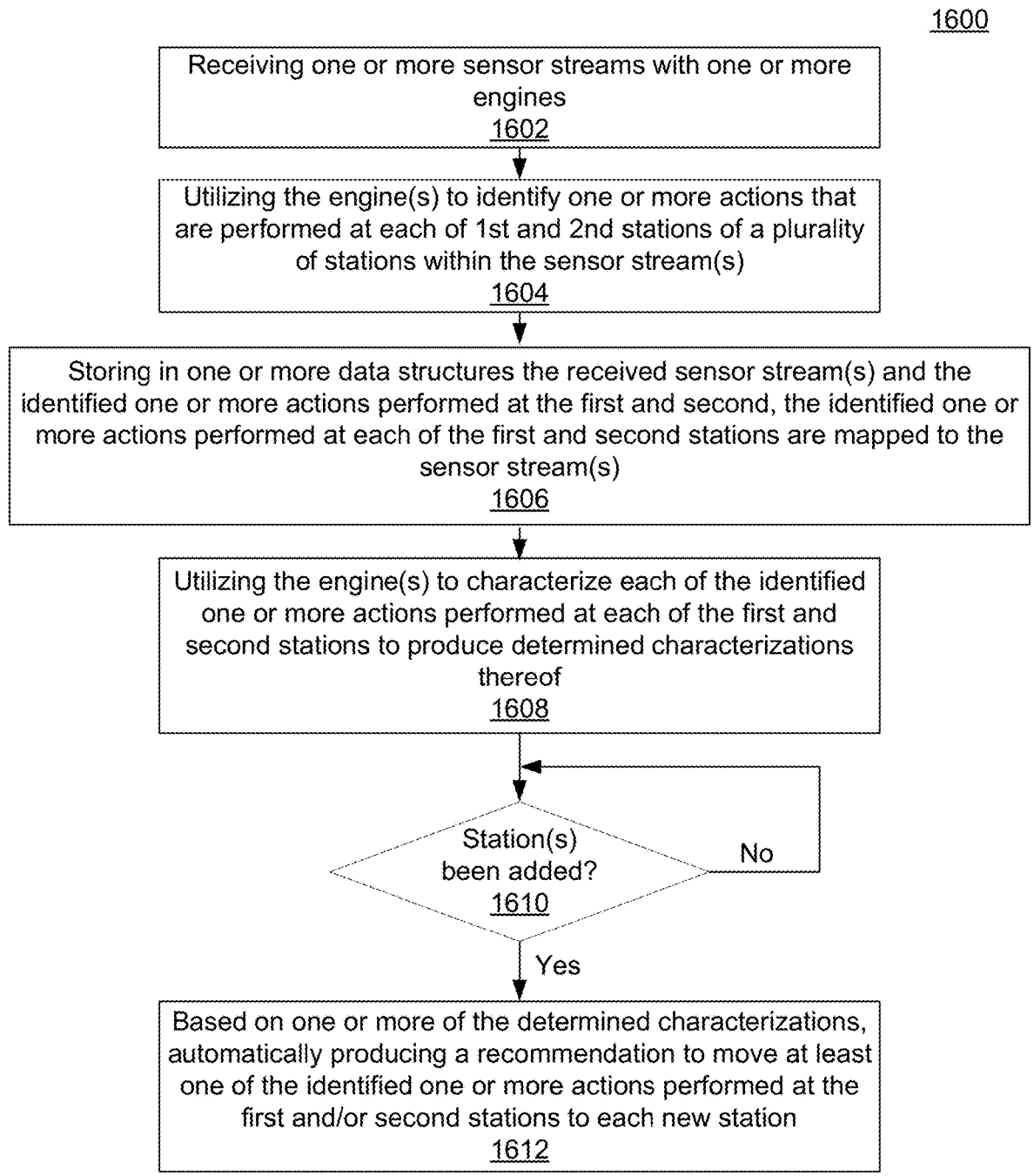
FIG. 16 is a flow chart of an exemplary method in accordance with various embodiments of the present disclosure.

FIG. 16 is a flow diagram of a method 1600 for dynamically rebalancing a line when one or more stations are added to the line in accordance with various embodiments of the present disclosure. Although specific operations are disclosed in FIG. 16, such operations are examples. The method 1600 may not include all of the operations illustrated by FIG. 16. Also, method 1600 may include various other operations and/or variations of the operations shown. Likewise, the sequence of the operations of flow diagram 1600 can be modified. It is appreciated that not all of the operations in flow diagram 1600 may be performed. In various embodiments, one or more of the operations of method 1600 can be controlled or managed by one or more engines (as described herein), by software, by firmware, by hardware or by any combination thereof, but is not limited to such. Method 1600 can include processes of various embodiments of the present disclosure which can be controlled or managed by a processor(s) and electrical components under the control of computer or computing device readable and executable instructions or code. The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory.

At operation 1602, one or more sensor streams can be received by one or more engines as described herein. It is noted that operation 1602 can be implemented in a wide variety of ways. For example, the one or more sensor streams at operation 1602 can include one or more of: video frames, thermal sensor data, force sensor data, audio sensor data, haptic data, and light sensor data, but is not limited to such. Furthermore, the one or more sensor streams at operation 1602 can be associated with a plurality of stations where one or more actions occur at each station, but are not limited to such. It is noted that operation 1602 can be implemented in any manner similar to that described and/or shown by the present disclosure, but is not limited to such.

At operation 1604 of FIG. 16, the one or more engines are utilized to identify one or more actions that are performed at each of first and second stations of a plurality of stations within the one or more sensor streams. It is noted that operation 1604 can be implemented in a wide variety of ways. For example, in various embodiments, the plurality of stations of method 1600 can be implemented as part of a production line, manufacturing, health care, warehousing, shipping, retail, or similar context, but is not limited to such. In addition, in various embodiments of method 1600, the first station can be sequentially after or before the second station of the plurality of stations. Furthermore, in various embodiments of method 1600, the first station and the second station of the plurality of stations are not sequential. Moreover, in various embodiments, each station of the plurality of stations of method 1600 can be understood as a location where one or more actions (e.g., sequential and/or non-sequential) occur. Furthermore, in various embodiments, the plurality of stations of method 1600 can include two or more stations. Note that operation 1604 can be implemented in any manner similar to that described and/or shown by the present disclosure, but is not limited to such.

At operation 1606, the received one or more sensor streams and the identified one or more actions performed at each of the first and second stations are stored in one or more data structures by the one or more engines. In addition, at operation 1606, it is noted that the identified one or more actions performed at each of the first and second stations are mapped or indexed to the one or more sensor streams by the one or more engines. Note that operation 1606 can be implemented in a wide variety of ways. For example, operation 1606 can be implemented in any manner similar to that described and/or shown by the present disclosure, but is not limited to such.

At operation 1608 of FIG. 16, the one or more engines are utilized to characterize each of the identified one or more actions performed at each of the first and second stations to produce determined characterizations thereof. Note that operation 1608 can be implemented in a wide variety of ways. For example, the determined characterizations at operation 1608 can include time taken to perform each of the identified one or more actions performed at each of the first and second stations. In addition, in various embodiments, the determined characterizations at operation 1608 can include at least one action of the identified one or more actions performed at the first station or second station cannot be moved because of one or more station capability constraints (e.g., equipment and/or physical limitations associated with one or more stations). Moreover, in various embodiments, the determined characterizations at operation 1608 can include at least one action of the identified one or more actions performed at the first station or second station cannot be moved because of one or more sequence constraints associated with one or more stations. Note that operation 1608 can be implemented in any manner similar to that described and/or shown by the present disclosure, but is not limited to such.

At operation 1610, a determination is made as to whether one or more stations have been added to the first and second stations of the line. If not, the method 1600 proceeds to the beginning of operation 1610 to repeat it. However, if it is determined at operation 1610 that one or more stations have been added to the first and second stations of the line, the method 1600 proceeds to operation 1612. Note that operation 1610 can be implemented in a wide variety of ways. For example, the determination at operation 1610 can be performed by one or more engines, but is not limited to such. It is noted that the operation 1610 can be implemented in any manner similar to that described and/or shown by the present disclosure, but is not limited to such.

At operation 1612 of FIG. 16, based on one or more of the determined characterizations, a recommendation is produced automatically by the one or more engines to move at least one of the identified one or more actions performed at the first and/or second stations to each newly added station. Note that operation 1612 can be implemented in a wide variety of ways. For example, in various embodiments at operation 1612, based on one or more of the determined characterizations, a recommendation is produced automatically by the one or more engines to move at least one of the identified one or more actions performed at the first station to each newly added station. Furthermore, in various embodiments at operation 1612, based on one or more of the determined characterizations, a recommendation is produced automatically by the one or more engines to move at least one of the identified one or more actions performed at the second station to each newly added station. In various embodiments, the recommendation at operation 1612 can be produced in real-time while a line is running or offline (or post-facto or on-demand) for later implementation. In various embodiments, the recommendation at operation 1612 can be produced either dynamically or post-facto, but is not limited to such. In various embodiments, the recommendation automatically produced at operation 1612 by the one or more engines can be implemented as a visual recommendation (e.g., via one or more displays, via the dashboard interface 1100 being displayed, and the like), as an audible recommendation (e.g., via one or more speakers), as a tactile recommendation, and the like, or any combination thereof, but is not limited to such. In addition, the one or more determined characterizations at operation 1612 can include the one or more of the determined characterizations described above with reference to operation 1610, but is not limited to such. It is noted that the operation 1612 can be implemented in any manner similar to that described and/or shown by the present disclosure, but is not limited to such.

Figure 17:
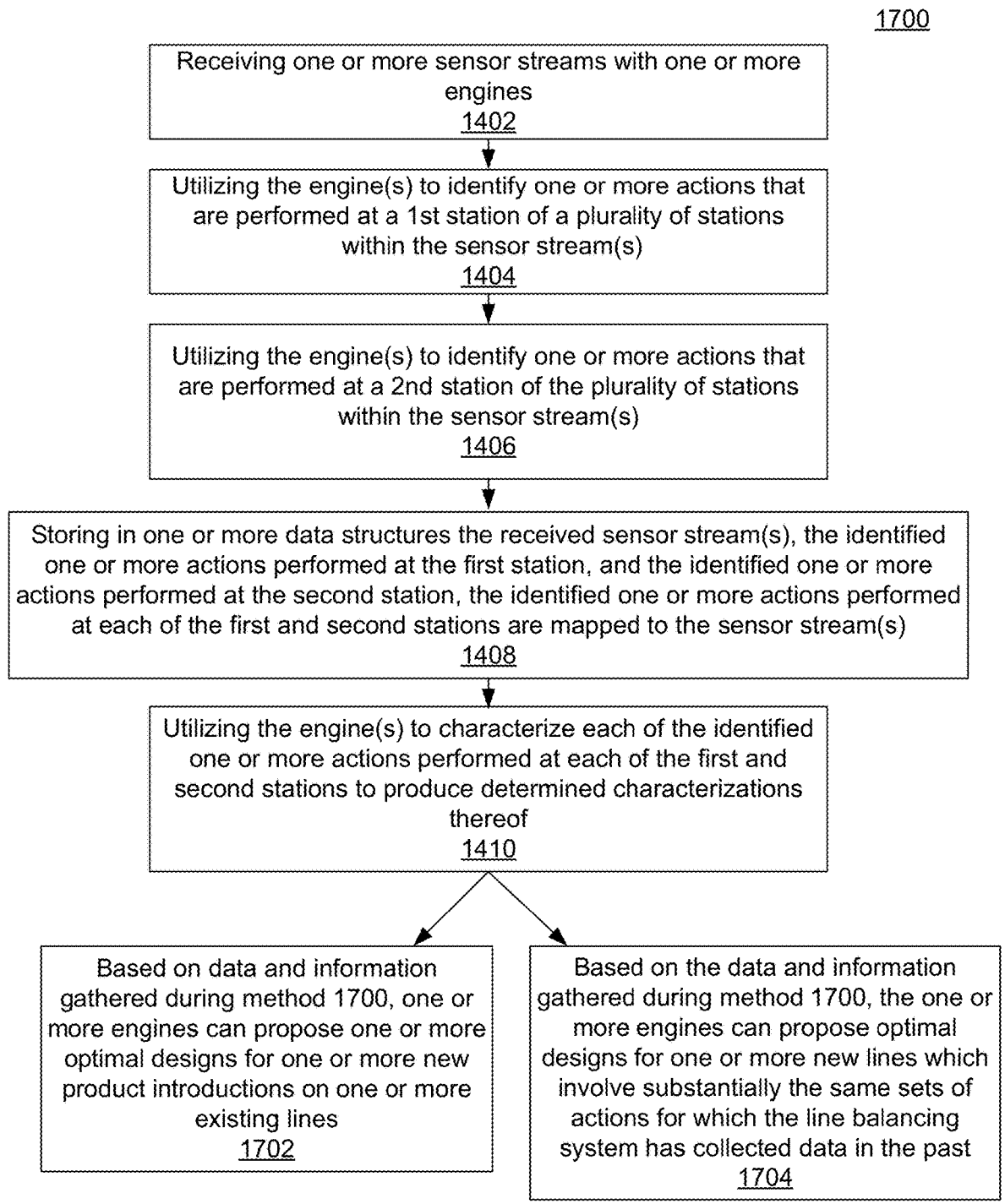
FIG. 17 is a flow chart of an exemplary method in accordance with various embodiments of the present disclosure.

FIG. 17 is a flow diagram of a method 1700 for line balancing and proposing more optimal designs for a new product introduction and/or for more optimal designs for new lines automatically in accordance with various embodiments of the present disclosure. Although specific operations are disclosed in FIG. 17, such operations are examples. The method 1700 may not include all of the operations illustrated by FIG. 17. Also, method 1700 may include various other operations and/or variations of the operations shown. Likewise, the sequence of the operations of flow diagram 1700 can be modified. It is appreciated that not all of the operations in flow diagram 1700 may be performed. In various embodiments, one or more of the operations of method 1700 can be controlled or managed by one or more engines (as described herein), by software, by firmware, by hardware or by any combination thereof, but is not limited to such. Method 1700 can include processes of various embodiments of the present disclosure which can be controlled or managed by a processor(s) and electrical components under the control of computer or computing device readable and executable instructions or code. The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory.

Note that operations 1402, 1404, 1406, 1408, and 1410 of FIG. 17 can be implemented in any manner similar to that described and/or shown by the operations 1402, 1404, 1406, 1408, and 1410 of method 1400 of FIG. 14.

After operation 1410 of FIG. 17, it is noted that method 1700 can perform operation 1702 and/or operation 1704.

At operation 1702, based on the data and information gathered during method 1700, one or more engines (as described herein) can propose one or more optimal designs for one or more new product introductions on one or more existing lines. Note that operation 1702 can be implemented in a wide variety of ways. For example, in various embodiments, operation 1702 can be implemented for an existing production line, manufacturing, health care, warehousing, shipping, retail, or similar context, but is not limited to such. Note that operation 1702 can be implemented in any manner similar to that described and/or shown by the present disclosure, but is not limited to such.

At operation 1704 of FIG. 17, based on the data and information gathered during method 1700, the one or more engines can propose optimal designs for one or more new lines which involve substantially the same sets of actions for which the line balancing system has collected data in the past. Note that operation 1704 can be implemented in a wide variety of ways. For example, in various embodiments, operation 1704 can be implemented for one or more new production lines, manufacturing, health care, warehousing, shipping, retail, or similar context, but is not limited to such. Note that operation 1704 can be implemented in any manner similar to that described and/or shown by the present disclosure, but is not limited to such.

Figure 18:
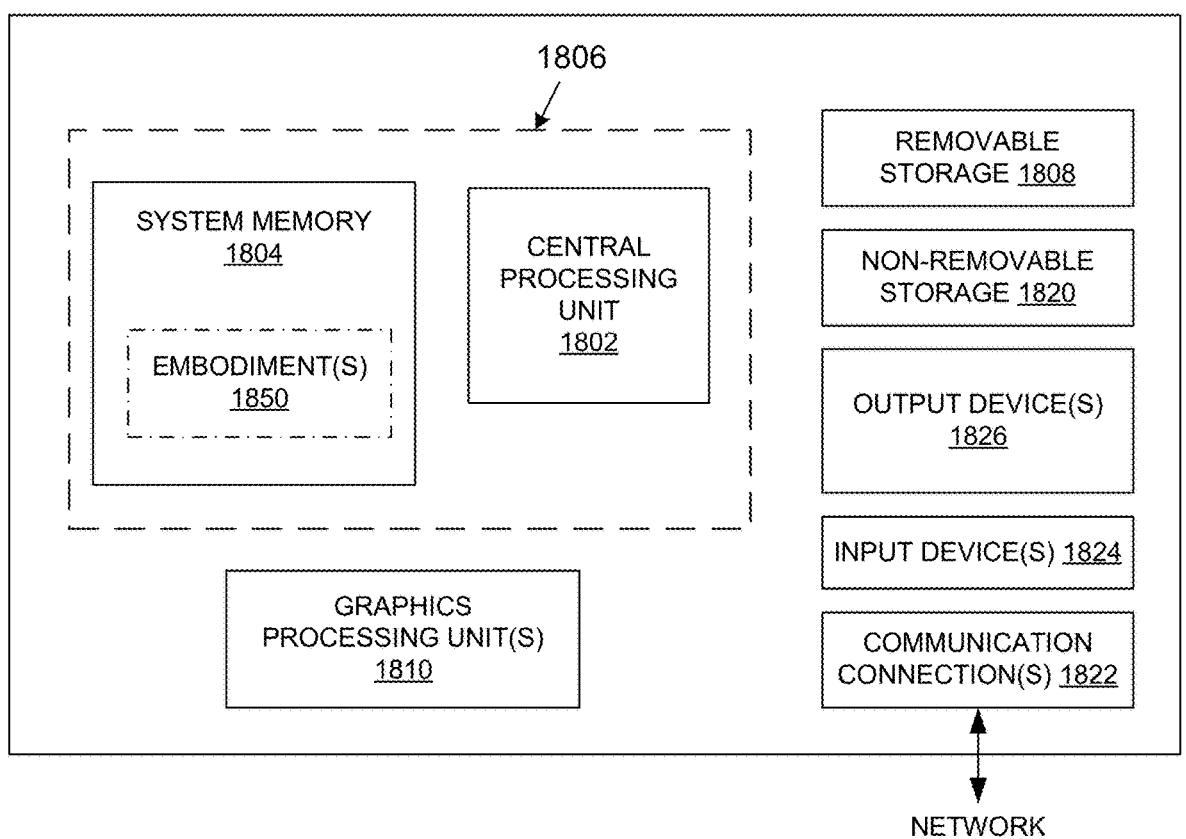
FIG. 18 shows a block diagram of an example of a computing system upon which one or more various embodiments described herein may be implemented in accordance with various embodiments of the present disclosure.

FIG. 18 shows a block diagram of an example of a computing system 1800 upon which one or more various embodiments described herein may be implemented in accordance with various embodiments of the present disclosure. In various embodiments, the computer system 1800 may include a cloud-based computer system, a local computer system, or a hybrid computer system that includes both local and remote devices. In a basic configuration, the system 1800 includes at least one processing unit 1802 and memory 1804. This basic configuration is illustrated in FIG. 18 by dashed line 1806. The system 1800 may also have additional features and/or functionality. For example, the system 1800 may include one or more Graphics Processing Units (GPUs) 1810. Additionally, the system 1800 may also include additional storage (e.g., removable and/or non-removable) including, but not limited to, magnetic or optical disks or tape. Such additional storage is illustrated in FIG. 18 by removable storage 1808 and non-removable storage 1820.

The system 1800 may also contain communications connection(s) 1822 that allow the device to communicate with other devices, e.g., in a networked environment using logical connections to one or more remote computers. Furthermore, the system 1800 may also include input device(s) 1824 such as, but not limited to, a voice input device, touch input device, keyboard, mouse, pen, touch input display device, etc. In addition, the system 1800 may also include output device(s) 1826 such as, but not limited to, a display device, speakers, printer, etc.

In the example of FIG. 18, the memory 1804 includes computer-readable instructions, data structures, program modules, and the like associated with one or more various embodiments 1850 in accordance with the present disclosure. However, the embodiment(s) 1850 may instead reside in any one of the computer storage media used by the system 1800, or may be distributed over some combination of the computer storage media, or may be distributed over some combination of networked computers, but is not limited to such.

It is noted that the computing system 1800 may not include all of the elements illustrated by FIG. 18. Moreover, the computing system 1800 can be implemented to include one or more elements not illustrated by FIG. 18. It is pointed out that the computing system 1800 can be utilized or implemented in any manner similar to that described and/or shown by the present disclosure, but is not limited to such.

The foregoing descriptions of various specific embodiments in accordance with the present disclosure have been presented for purposes of illustration and description. They are not intended to be exhaustive or to limit the present disclosure to the precise forms disclosed, and many modifications and variations are possible in light of the above teaching. The various embodiments were chosen and described in order to best explain the principles of the present disclosure and its practical application, to thereby enable others skilled in the art to best utilize the present disclosure and various embodiments with various modifications as are suited to the particular use contemplated. The present disclosure is to be construed according to the Claims and their equivalents.

What is claimed is:

1. A method comprising:
receiving one or more sensor streams including one or more video frame streams with an engine;
utilizing the engine to identify one or more actions from the one or more video frame streams that are performed on a product at a first station of a plurality of stations;
utilizing the engine to identify one or more actions from the one or more video frame streams that are performed on the product at a second station of the plurality of stations;
storing in a data structure the received one or more sensor streams, the identified one or more actions performed on the product at the first station, and the identified one or more actions performed on the product at the second station, wherein the identified one or more actions performed on the product at each of the first and second stations are mapped to the one or more sensor streams;
utilizing the engine to characterize each of the identified one or more actions performed on the product at each of the first and second stations to produce determined characterizations thereof, wherein the determined characterizations include time taken to perform the one or more actions performed at each of the first and second stations; and
based on one or more of the determined characterizations, automatically producing a recommendation, either dynamically or post-facto, to move at least one of the identified one or more actions performed on the product at the second station to the first station to reduce cycle time.

2. The method of claim 1, wherein the recommendation would result in elimination of the second station.

3. The method of claim 1, wherein the first and second stations are non-sequential.

4. The method of claim 1, wherein the one or more of the determined characterizations comprise at least one action of the identified one or more actions performed at the second station cannot be moved because of a station capability constraint associated with the second station.

5. The method of claim 1, wherein the one or more of the determined characterizations comprise a sequence constraint of the identified one or more actions performed at the second station.

6. The method of claim 1, wherein the one or more sensor streams further include thermal sensor data.

7. The method of claim 1, wherein the one or more sensor streams further include force sensor data.

8. The method of claim 1, wherein the one or more sensor stream further include audio sensor data.

9. The method of claim 1, wherein the one or more sensor streams further include light sensor data.

10. The method of claim 1, wherein the one or more sensor streams further include haptic data.

11. The method of claim 1, further comprising:
utilizing the engine to propose one or more optimal designs for a new product introduction on an existing line.

12. The method of claim 1, further comprising:
utilizing the engine to propose one or more optimal designs for one or more new lines comprising one or more actions that are the same as one or more of the identified actions performed at the first and second stations.

13. The method of claim 1, further comprising:
utilizing the engine to identify the one or more actions from one or more further sensor streams that are performed at the first or second station.

14. The method of claim 1, wherein the determined characterizations include a start and stop location of the one or more actions performed at each of the first and second stations.

15. A system comprising:
one or more sensors;
a data storage unit; and
an engine coupled to the one or more sensors and the data storage unit, the engine configured to:
receive one or more sensor streams from the one or more sensors;
identify one or more actions that are performed on a product at a first station of a plurality of stations from video frames of the one or more sensor streams;
identify one or more actions that are performed on the product at a second station of the plurality of stations from video frames of the one or more sensor streams;
store the received sensor stream, the identified one or more actions performed at the first station, and the identified one or more actions performed on the product at the second station in one or more data structures on the data storage unit, wherein the identified one or more actions performed on the product at each of the first and second stations are mapped to the sensor stream;
characterize each of the identified one or more actions performed on the product at each of the first and second stations to produce determined characterizations thereof including time taken to perform the one or more actions performed on the product at each of the first and second stations; and
based on one or more of the determined characterizations, automatically produce a recommendation, either dynamically or post-facto, to move at least one of the identified one or more actions performed on the product at the second station to the first station to reduce cycle time.

16. The system of claim 15, further comprising:
a network configured to communicatively couple the one or more sensors, the engine, and the data storage unit.

17. The system of claim 16, further comprising:
a data compression unit communicatively coupled between the one or more sensors and the network, the data compression unit configured to compress the data of the sensor stream before transmission across the network.

18. The system of claim 15, wherein the recommendation would eliminate the second station.

19. The system of claim 15, wherein the one or more of the determined characterizations further includes at least one action of the identified one or more actions performed at the second station cannot be moved because of equipment or physical limitations associated with the second station.

20. The system of claim 15, wherein the one or more of the determined characterizations further includes a sequence constraint of the identified one or more actions performed at the second station.

21. The system of claim 15, wherein the one or more sensor streams further includes at least one of thermal sensor data, force sensor data, audio sensor data, and light sensor data.

22. The system of claim 15, further comprising:
identifying the one or more actions that are performed at the first or second station from one or more further sensor streams.

23. The system of claim 21, further comprising:
utilizing the one or more engines to further identify the one or more actions from one or more further sensor streams.

24. One or more non-transitory computing device-readable storage mediums storing instructions executable by one or more engines to perform a method comprising:
receiving one or more sensor streams with the one or more engines, wherein the one or more sensor streams include one or more video streams;
utilizing the one or more engines to identify one or more actions from the one or more video streams that are performed on a product at a first station of a plurality of stations of a production line;
utilizing the one or more engines to identify one or more actions from the one or more video streams that are performed on the product at a second station of the plurality of stations of the production line;
storing in one or more data structures the received one or more sensor streams, the identified one or more actions performed on the product at the first station, and the identified one or more actions performed on the product at the second station, the identified one or more actions performed on the product at each of the first and second stations are mapped to the one or more sensor streams;
utilizing the one or more engines to characterize each of the identified one or more actions performed on the product at each of the first and second stations to produce determined characterizations thereof, wherein the determined characterizations include time taken to perform each of the one or more actions performed on the product at each of the first and second stations; and
based on one or more of the determined characterizations, automatically producing a recommendation, either dynamically or post-facto, with the one or more engines to move at least one of the identified one or more actions performed on the product at the second station to the first station to reduce cycle time of the production line.

* * * * *